United States Patent [19]
Gluchowski et al.

[11] Patent Number: 5,990,128
[45] Date of Patent: Nov. 23, 1999

[54] $\alpha_{1C}$ SPECIFIC COMPOUNDS TO TREAT BENIGN PROSTATIC HYPERPLASIA

[75] Inventors: Charles Gluchowski, Wayne; Carlos C. Forray, Paramus; George Chiu, Bridgewater; Theresa A. Branchek, Teaneck; John M. Wetzel, Elmwood Park; Paul R. Hartig, Pennington, all of N.J.

[73] Assignee: Synaptic Pharmaceutical Corporation, Paramus, N.J.

[21] Appl. No.: 08/722,190

[22] PCT Filed: Apr. 4, 1995

[86] PCT No.: PCT/US95/04203

§ 371 Date: Nov. 22, 1996

§ 102(e) Date: Nov. 22, 1996

[87] PCT Pub. No.: WO95/28157

PCT Pub. Date: Oct. 26, 1995

Related U.S. Application Data

[63] Continuation-in-part of application No. 08/228,932, Apr. 13, 1994, Pat. No. 5,578,611.

[51] Int. Cl.$^6$ ........................ A61K 35/445; A61K 35/135
[52] U.S. Cl. ............................... 514/318; 514/654
[58] Field of Search ..................... 514/318, 654

[56] References Cited

U.S. PATENT DOCUMENTS

| | | | |
|---|---|---|---|
| 4,975,440 | 12/1990 | Flockerzi et al. | 514/318 |
| 4,994,461 | 2/1991 | Ulrich | 514/252 |
| 5,403,842 | 4/1995 | Leonardi et al. | 514/252 |
| 5,403,847 | 4/1995 | Gluchowski et al. | 514/318 |
| 5,508,306 | 4/1996 | Chiu et al. | 514/524 |
| 5,556,753 | 9/1996 | Bard et al. | 435/6 |
| 5,578,611 | 11/1996 | Gluchowski et al. | 514/318 |

FOREIGN PATENT DOCUMENTS

| | | |
|---|---|---|
| 0176956 | 4/1986 | European Pat. Off. . |
| 2144080 | 3/1972 | Germany . |
| 3709796 | 11/1987 | Germany . |
| 8907443 | 8/1989 | WIPO . |
| WO9118599 | 12/1991 | WIPO . |
| WO9421660 | 9/1994 | WIPO . |

OTHER PUBLICATIONS

Archibald, et al., "Penzamidopiperidines. 3. Carbocyclic Derivatives Related to Indoramin" *J. Med. Chem.* (1974) 17(7): 739–744.

Chapple, C., "Medical Treatment for Benign Prostatic Hyperplasia" *B.M.J.* (1992) 304: 1198–1199.

Chow, et al., "Multicentre Controlled Trial of Indoramin in the Symptomatic Relief of Benign Prostatic Hypertrophy" *Br. J. Urology* (1990) 65(1): 36–38.

Christmas, T.J. and Kirby, R.S., "Alpha–Adrenoceptor Blockers in the Treatment of Bening Prostatic Hyperplasia" *World J. Urol.* (1991) 9: 36–40.

Heimbach, et al., "Anwendung Von α–Rezeptorenblockern Bei Urologischen Erkrankungen" *Dtsch. Med. Wochenschr.* (1992) 117(21): 825–828.

Lepor H., et al., "The Alpha–Adrenoceptor Subtype Mediating the Tension of Human Prostatic Smooth Muscle" *The Prostate* (1993) 22:301–307.

Lepor, et al., "Laboratory Assessment of Terazosin and Alpha–1 Blockade in Prostatic Hyperplasia" *Urology* (1988) 32(6): 21–26.

Kaminka, M.E., et al., "Effect of Prazosin on Human Benign Prostatic Hyperplasia Strips" *Chemical Abstracts* (1998) Abstract No. 563185.

Yamada, et al., "Alpha–1 Adrenoceptors in Human Prostate: Characterization and Alternation in Benign Prostatic Hypertrophy" *Chemical Abstracts* (1987) Abstract No. 513718.

Marshall, I., et al., "Human α1C–Adrenoceptor: Functional Characterization In Prostate," Meeting of the British Pharmacological Society (1992), Abst. No. 372P.

Archibald, J.L., et al., "Antihypertensive Ureidopiperidines," Journal of Medicinal Chemistry, 23: 857–861 (1980).

Boer, R., et al., "(+)–Niguldipine binds with very high affinity to $Ca^{2+}$ channels and to a subtype of $\alpha_1$–adrenoreceptors," European Journal of Pharmacological—Molecular Pharmacology Section, 172: 131–145 (1989); The Netherlands.

Forray, C., et al., "The 60 $_{1C}$ –Adrenergic Receptor that Meditates Smooth Muscle Contraction in Human Prostate Has the Pharmacological Properties of the Cloned Human 1cSubtype," Molecular Pharmacology, 45: 703–708 (1994); U.S.A..

(List continued on next page.)

*Primary Examiner*—Kimberly Jordan
*Attorney, Agent, or Firm*—John P. White; Cooper & Dunham LLP

[57] ABSTRACT

This invention provides a method of treating benign prostatic hyperplasia in a subject which comprises administering to the subject a therapeutically effective amount of an $\alpha_{1C}$ antagonist which (a) binds to a human $\alpha_{1C}$ adrenergic receptor with a binding affinity greater than 100-fold higher than the binding affinity with which the $\alpha_{1C}$ antagonist binds to a human $\alpha_{1A}$ adrenergic receptor, a human $\alpha_{1B}$ adrenergic receptor, and a human histamine $H_1$ receptor; and (b) binds to a human $\alpha_2$ adrenergic receptor with a binding affinity which is greater than 100-fold lower than the binding affinity with which the $\alpha_{1C}$ antagonist binds to such $\alpha_{1C}$ adrenergic receptor.

The invention further provides a method of inhibiting contraction of a prostate tissue which comprises contacting the prostate tissue with an effective contraction-inhibiting amount of an $\alpha_{1C}$ antagonist which (a) binds to a human $\alpha_{1C}$ adrenergic receptor with a binding affinity greater than 100-fold higher than the binding affinity with which the $\alpha_{1C}$ antagonist binds to a human $\alpha_{1A}$ adrenergic receptor, a human $\alpha_{1B}$ adrenergic receptor, and a human histamine $H_1$ receptor; and (b) binds to a human $\alpha_2$ adrenergic receptor with a binding affinity which is greater than 100-fold lower than the binding affinity with which the $\alpha_{1C}$ antagonist binds to such $\alpha_{1C}$ adrenergic receptor.

20 Claims, 2 Drawing Sheets

OTHER PUBLICATIONS

Forray, C., Chiu, G., et al., "Effects of Novel Alpha–1C Adrenergic Receptor Antagonists on the Contraction of Human Prostate Smmoth Muscle," American Urological Association Eighty–ninth Annual Meeting, May 14–19, 1994 The Journal of Urology, 151(5), Abstract #159 May 1994; U.S.A.

Forray, C., Bard, J.A., et al., "Comparison of the Pharmacological Properties of the Cloned Bovine, Human, and Rat α1C–Adrenergic Receptors," The FASEB Journal, 8(4), Abstract #2042 (1994); U.S.A.

Gong, E., et al., "α1C–Adrenergid Antagonists and Orthostatic Hypotension in the Rat," The FASEB Journal, 8(4), Abstract #2043 (1994); U.S.A.

Gup, et al., "Autonomic Receptors in Human Prostate Adenomas," Journal of Urology (1990) 143(1); 179–185.

Hieble, J.P., et al., "In Vitro characterization of the α1–adrenoreceptors in human prostate," European Journal of Pharmacology, 107: 111–117 (1985); The Netherlands.

Lepor, H., et al., "Localization of Alpha $_{1C}$ Adrenoceptor ($α_{1C}$ AR) Subtypes in the Human Prostate," American Urological Association Eighty–Ninth Annual Meeting, May 14–19, 1994, The Journal of Urology, 151 (5), Abstract #614 (May 1994); U.S.A.

Lepor and Baumann, et al., Medline Abstracts (1988), Abst. No. 88317113; "The Alpha Adrenergic Binding Properties of Terazosin in the Human Prostate Adenoma and Canine Brain," Journal of Urology (1988), 140(3): 664–667.

Lepor and Knapp–Maloney, et al., "A Dose Titration Study Evaluating Terazosin, A Selective Once–a–Day Alpha–1–Blocker for the Treatment of Symptomatic Benign Prostatic Hyperplasia," Journal of Urology (1990) 144(6); 1393–1398.

Lepor and Shapiro, et al., Medline Abstracts (1988), Abst. No. 88317114; "The Effect of Electrocautery on Neurotransmitter Receptor Binding Assays in the Canine Prostate," Journal of Urology (1988), 140(3): 668–671.

Lomasney, J.W., et al., "Molecular Cloning and Expression of the cDNA for the α1A–Adrenergic Receptor," Journal of Biological Chemistry, 266: 6365–6369 (1991).

Perez, J.L., et al., "Is the $α_{1C}$–Adrenergic Receptor the $α_{1A}$–Subtype?" The FASEB Journal, 8(4), Abstract #2041 (1994); U.S.A.

Ramaro, C.S., et al., "Genomic Organization and Expression of the Human $α_{1B}$–Adrenergic Receptor," Journal of Biological Chemistry (1992), 267(30): 21936–21944.

Tang, R., et al., "Localization of Alpha 1C Adrenoceptor ( 1 AR) Subtypes in the Human Prostatic Tissue," The FASEB Journal, 8(5), Abstract #5070 (1994); U.S.A..

Wetzel, J.M., et al., "Structural and Functional Studies of the Human $α_{1C}$Adrenergic Receptor: The Orientation of Transmembrane Helix 5," The FASEB Journal, 8(4), Abst. #2182(1994), U.S.A.

Yamada, S., et al., "$α_{1A}$–Adrenergic Receptors in Human Prostate: Characterization and alteration in Benign Prostatic Hypertrophy,"Journal of Pharmacology and Experimental Therapeutics, 242: 326–330 (1987).

$\alpha_{1C}$ SPECIFIC COMPOUNDS TO TREAT BENIGN PROSTATIC HYPERPLASIA

This application is a 371 national stage filing of PCT/US95/04203, filed Apr. 4, 1995, which is a CIP of 08/228,932, filed Apr. 13, 1994, now U.S. Pat. No. 5,578,611, the contents of which are hereby incorporated by reference.

BACKGROUND OF THE INVENTION

Benign Prostatic Hyperplasia (BPH), also called Benign Prostatic Hypertrophy, is a progressive condition which is characterized by a nodular enlargement of prostatic tissue resulting in obstruction of the urethra. This results in increased frequency of urination, nocturia, a poor urine stream and hesitancy or delay in starting the urine flow. Chronic consequences of BPH can include hypertrophy of bladder smooth muscle, a decompensated bladder and an increased incidence of urinary tract infection. The specific biochemical, histological and pharmacological properties of the prostate adenoma leading to the bladder outlet obstruction are not yet known. However, the development of BPH is considered to be an inescapable phenomenon for the aging male population. BPH is observed in approximately 70% of males over the age of 70. Currently, in the United States, the method of choice for treating BPH is surgery (Lepor, H., Urol. Clinics North Amer., 17, 651 (1990)). Over 400,000 prostatectomies are performed annually (data from 1986). A medicinal alternative to surgery is clearly very desirable. The limitations of surgery for treating BPH include the morbidity rate of an operative procedure in elderly men, persistence or recurrence of obstructive and irritative symptoms, as well as the significant cost of surgery. α-Adrenergic receptors are specific neuroreceptor proteins located in the peripheral and central nervous systems on tissues throughout the body. These receptors are important switches for controlling many physiological functions and, thus, represent important targets for drug development. In fact, many α-adrenergic drugs have been developed over the past 40 years. Examples include clonidine, phenoxybenzamine and prazosin (treatment of hypertension), naphazoline (nasal decongestant), and apraclonidine (treating glaucoma). α-Adrenergic drugs can be broken down into two distinct classes: agonists (clonidine and naphazoline are agonists), which mimic the receptor activation properties of the endogenous neurotransmitter norepinephrine, and antagonists (phenoxybenzamine and prazosin are antagonists), which act to block the effects of norepinephrine. Many of these drugs are effective but also produce unwanted side effects (for example, clonidine produces dry mouth and sedation in addition to its antihypertensive effects).

During the past 15 years a more precise understanding of α-adrenergic receptors and their drugs has evolved through increased scientific scrutiny. Prior to 1977, only one α-adrenergic receptor was known to exist. Between 1977 and 1988, it was accepted by the scientific community that at least two α-adrenergic receptors—$\alpha_1$ and $\alpha_2$—existed in the central and peripheral nervous systems. Since 1988, new techniques in molecular biology have led to the identification of at least six α-adrenergic receptors which exist throughout the central and peripheral nervous systems: $\alpha_{1A}$, $\alpha_{1B}$, $\alpha_{1C}$, $\alpha_{2A}$, $\alpha_{2B}$ and $\alpha_{2C}$ (Bylund, D. B., FASEB J., 6, 832 (1992)). It is not known precisely which physiological responses in the body are controlled by each of these receptors. In addition, many α-adrenergic drugs that were developed before 1992 are not selective for any particular α-adrenergic receptor. Many of these drugs produce untoward side effects which may be attributed to their poor α-adrenergic receptor selectivity.

Since the mid 1970's, nonselective α-antagonists have been prescribed to treat BPH. In 1976, M. Caine, et al. (Brit. J. Urol., 48, 255 (1976)), reported that the nonselective α-antagonist phenoxybenzamine was useful in relieving the symptoms of BPH. This drug may produce its effects by interacting with α-receptors located on the prostate. However, this drug also produces significant side effects which severely limit its use in treating patients on a chronic basis. More recently, the α-adrenergic antagonists prazosin and terazosin have also been found to be useful for treating BPH. However, these drugs also produce untoward side effects. The most recently approved drug Proscar™ (Merck) prescribed for BPH is not an α-adrenergic antagonist, but rather acts by blocking 5-α-reductase. While Proscar is able to relieve symptoms, it is effective in only 30% of all patients, and requires a period of up to 6 months to show results.

From binding studies using cloned rat $\alpha_{1A}$, hamster $\alpha_{1B}$, and bovine $\alpha_{1C}$ receptors, and functional studies of antagonism in vitro using human prostate, I. Marshall, et al., concluded that the receptor mediating contraction of the human prostrate is of the $\alpha_{1C}$ subtype (Marshall, I., et al., Brit. Pharmacol. Soc., (1992)).

Furthermore, using cloned human receptors the binding characteristics of the known BPH drugs to various receptor subtypes have been determined, as described more fully hereinafter. Based upon such binding information and additional data, it has been observed that the side effects which occur with the drugs prazosin and terazosin may be due to their poor selectivity for specific α-adrenergic receptors. In contrast, indoramin is a drug which is slightly selective for the human $\alpha_{1C}$ receptor relative to the other human α-adrenergic receptors, but it also interacts at human histamine H1 receptors. This compound produces untoward side effects which may be attributed to its activity at such $H_1$ receptors.

It would be desirable to provide methods and compounds which allow the treatment of BPH but which avoid the production of side effects observed for all currently used medications.

From the binding information described hereinafter, it has unexpectedly been discovered that compounds which are specific for an $\alpha_{1C}$ adrenergic receptor with a binding affinity greater than ten-fold higher than the binding affinity with which the compounds bind to an $\alpha_{1A}$ adrenergic receptor, a human $\alpha_{1B}$ adrenergic receptor, and a human histamine $H_1$ receptor, and (b) bind to an $\alpha_2$ adrenergic receptor with a binding affinity which is greater than ten-fold lower than the binding affinity with which the compounds bind to such $\alpha_{1C}$ adrenergic receptor are effective for the treatment of BPH.

Furthermore, we have characterized several antagonists selective for the $\alpha_{1C}$ adrenergic receptor using a rat orthostatic hypotension model to ascertain the vascular effects of drugs which may be indicative of their ability to produce dizziness in patients, and observed that while nonselective alpha 1 antagonists produce significant effects on orthostatic hypotension, selective alpha 1c antagonists do not produce significant effects.

SUMMARY OF THE INVENTION

The subject invention provides a method of treating benign prostatic hyperplasia or inhibiting contraction of a prostate tissue in a subject in need thereof which comprises administering to the subject a therapeutically effective amount of an $\alpha_{1C}$ antagonist which binds to a human $\alpha_{1c}$ adrenergic receptor with a binding affinity greater than 50-fold higher than the binding affinity with which the $\alpha_{1C}$ antagonist binds to a human $\alpha_{1b}$ adrenergic receptor, provided that the $\alpha_{1C}$ antagonist is not 2,6-Dimethyl-4-(4-nitrophenyl)-1,4-dihydropyridine-3,5-dicarboxylic acid N-[3-(4,4-diphenylpiperdin-1-yl)propyl] amide ester hydrochloride hydrate.

BRIEF DESCRIPTION OF THE FIGURES

FIG. 1 illustrates compounds which are potent antagonists of the cloned human $\alpha_{1C}$ receptor.

Figure 1:
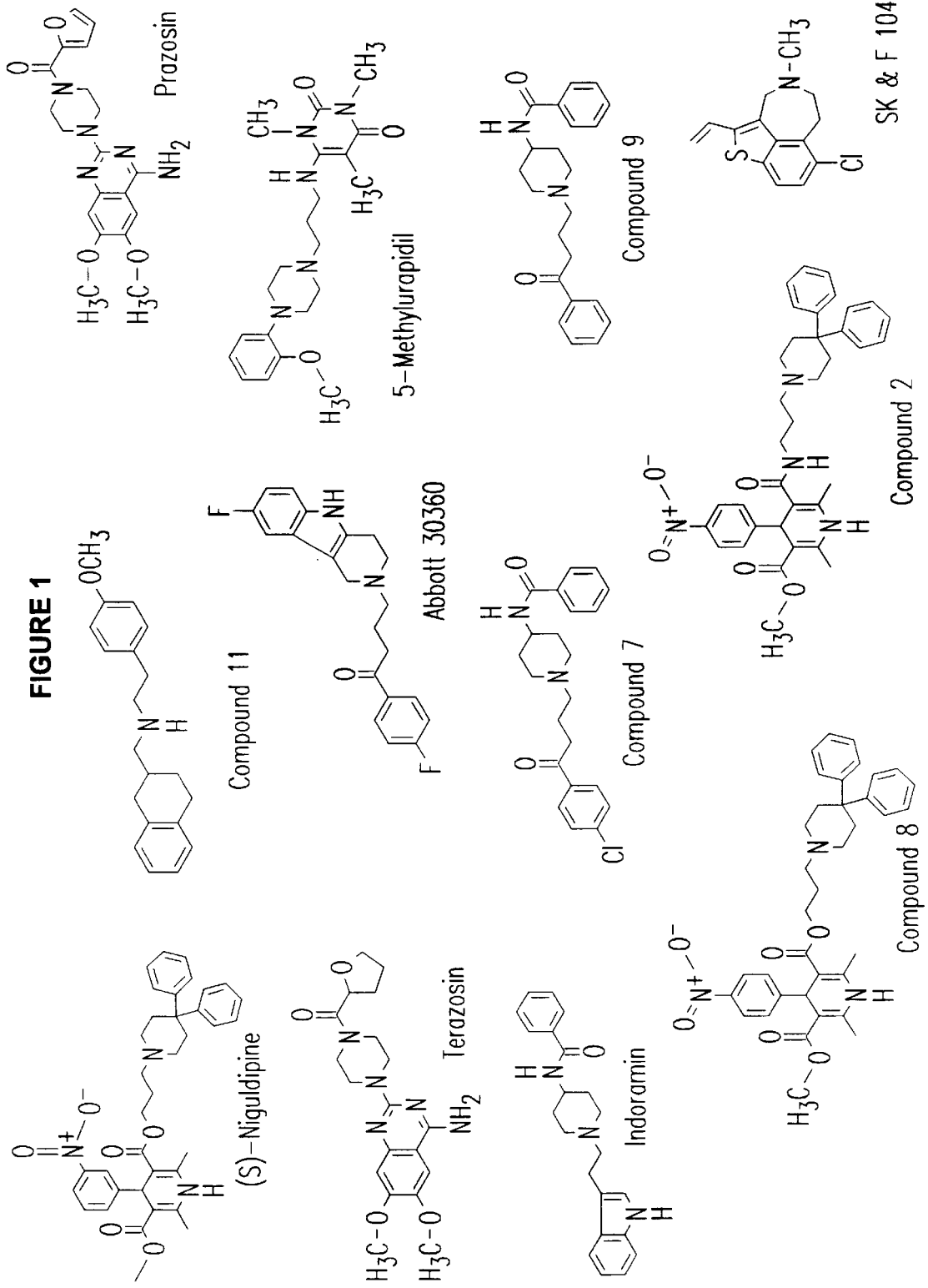
FIG. 1

Panel A illustrates the correlation of inhibition constants (pK$_i$) for a series of $\alpha_1$ antagonists at the cloned human $\alpha_{1A}$ receptors with efficiency of blocking contraction of human prostate tissue (pA$_2$).

Panel B illustrates the correlation of inhibition constants (pK$_1$) for a series of $\alpha_1$ antagonists at the cloned human $\alpha_{1B}$ receptors with efficiency of blocking contraction of human prostate tissue (pA$_2$).

Panel C illustrates the correlation of inhibition constants (pK$_1$) for a series of $\alpha_1$ antagonists at the cloned human $\alpha_{1C}$ receptors with efficiency of blocking contraction of human prostate tissue (pA$_2$).

DETAILED DESCRIPTION OF THE INVENTION

The present invention provides a method of treating benign prostatic hyperplasia or inhibiting contraction of a prostate tissue in a subject in need thereof which comprises administering to the subject a therapeutically effective amount of an $\alpha_{1C}$ antagonist which binds to a human $\alpha_{1c}$ adrenergic receptor with a binding affinity greater than 50-fold higher than the binding affinity with which the $\alpha_{1C}$ antagonist binds to a human $\alpha_{1b}$ adrenergic receptor, provided that the $\alpha_{1C}$ antagonist is not 2,6-Dimethyl-4-(4-nitrophenyl)-1,4-dihydropyridine-3,5-dicarboxylic acid N-[3-(4,4-diphenylpiperdin-1-yl)propyl] amide ester hydrochloride hydrate.

In a preferred embodiment, the $\alpha_{1C}$ antagonist used to practice the method of the invention additionally binds to a human $\alpha_{1a}$ adrenergic receptor, a human $\alpha_2$ adrenergic receptor and a human histamine H$_1$ receptor with a binding affinity which is greater than ten-fold lower than the binding affinity with which the $\alpha_{1C}$ antagonist binds to the $\alpha_{1c}$ adrenergic receptor.

Desirably, the $\alpha_{1C}$ antagonist used to practice the method of the invention additional binds to the human $\alpha_{1c}$ adrenergic receptor with a binding affinity greater than 75-fold higher than the binding affinity with which the $\alpha_{1C}$ antagonist binds to the human $\alpha_{1b}$ adrenergic receptor.

Alternatively or incrementally, the $\alpha_{1C}$ antagonist used to practice the method of the invention additionally binds to a human $\alpha_{1a}$ adrenergic receptor, a human $\alpha_2$ adrenergic receptor and a human histamine H$_1$ receptor with a binding affinity which is greater than ten-fold lower than the binding affinity with which the $\alpha_{1C}$ antagonist binds to the $\alpha_{1c}$ adrenergic receptor.

Alternatively or incrementally, the $\alpha_{1C}$ antagonist used to practice the method of the invention additionally binds to a calcium channel with a binding affinity which is greater than ten-fold lower than the binding affinity with which the $\alpha_{1c}$ antagonist binds to the $\alpha_{1c}$ adrenergic receptor.

Alternatively or incrementally, the $\alpha_{1C}$ antagonist used to practice the method of the invention additionally binds to a human dopamine D$_2$ or human histamine H$_2$ receptor with a binding affinity which is greater than ten-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to any serotonin receptor with a binding affinity which is greater than ten-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to a dopamine D$_3$, D$_4$ or D$_5$ receptor with a binding affinity which is greater than ten-fold lower than the binding affinity with which the $\alpha_{1C}$ antagonist binds to the $\alpha_{1C}$ adrenergic receptor.

In one embodiment, the $\alpha_{1C}$ antagonist used to practice the method of the invention additionally does not cause a fall in blood pressure at dosages effective to alleviate benign prostatic hyperplasia or contraction of the prostate tissue.

In a preferred embodiment the $\alpha_{1C}$ antagonist used to practice the method of the invention additionally does not cause a fall in blood pressure in rats at a dosage of 10 micrograms of $\alpha_{1C}$ antagonist per kilogram per rat.

A preferred embodiment the invention provides for a method of treating benign prostatic hyperplasia or inhibiting contraction of prostate tissue in a subject in need thereof which comprises administering to the subject a therapeutically effective amount of an $\alpha_{1C}$ antagonist which binds to a human $\alpha_{1c}$ adrenergic receptor with a binding affinity greater than 100-fold higher than the binding affinity with which the $\alpha_{1C}$ antagonist binds to a human $\alpha_{1b}$ adrenergic receptor and a human histamine H$_1$ receptor.

Alternatively or incrementally, the $\alpha_{1C}$ antagonist used to practice the method of the invention additionally binds to a human $\alpha_{1a}$ adrenergic receptor and a human $\alpha_2$ adrenergic receptor with a binding affinity which is greater than ten-fold lower than the binding affinity with which the $\alpha_{1C}$ antagonist binds to the $\alpha_{1c}$ adrenergic receptor.

Desirably, the $\alpha_{1C}$ antagonist used to practice the method of the invention additional binds to a calcium channel with a binding affinity which is greater than ten-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to a human dopamine D$_2$ or human histamine H$_2$ receptor with a binding affinity which is greater than ten-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to any serotonin receptor with a binding affinity which is greater than ten-fold lower than the binding affinity with which the $\alpha_{1C}$ adrenergic receptor.

Alternatively or incrementally, the $\alpha_{1C}$ antagonist used to practice the method of the invention additionally binds to a dopamine D$_3$, D$_4$ or D$_5$ receptor with a binding affinity which is greater than ten-fold lower than the binding affinity with which the $\alpha_{1C}$ antagonist binds to the $\alpha_{1C}$ adrenergic receptor.

In one embodiment, the $\alpha_{1C}$ antagonist used to practice the method of the invention additionally does not cause a fall in blood pressure at dosages effective to alleviate benign prostatic hyperplasia or contraction of the prostate tissue.

In a preferred embodiment the $\alpha_{1C}$ antagonist used to practice the method of the invention additionally does not cause a fall in blood pressure in rats at a dosage of micrograms of $\alpha_{1C}$ antagonist per kilogram per rat.

In a preferred embodiment the invention provides for a method of treating benign prostatic hyperplasia in a subject which comprises administering to the subject a therapeutically effective amount of an $\alpha_{1C}$ antagonist which:

a. binds to a human $\alpha_{1C}$ adrenergic receptor with a binding affinity greater than 100-fold higher than the binding affinity with which the $\alpha_{1C}$ antagonist binds to a human $\alpha_{1A}$ adrenergic receptor, a human $\alpha_{1B}$ adrenergic receptor, and a human histamine $H_1$ receptor; and b. binds to a human $\alpha_2$ adrenergic receptor with a binding affinity which is greater than 100-fold lower than the binding affinity with which the $\alpha_{1C}$ antagonist binds to such $\alpha_{1C}$ adrenergic receptor.

In a preferred embodiment of the invention provides for a method of inhibiting contraction of a prostate tissue which comprises contacting the prostate tissue with an effective contraction-inhibiting amount of an $\alpha_{1C}$ antagonist which:

a. binds to a human $\alpha_{1C}$ adrenergic receptor with a binding affinity greater than 100-fold higher than the binding affinity with which the $\alpha_{1C}$ antagonist binds to a human $\alpha_{1A}$ adrenergic receptor, a human $\alpha_{1B}$ adrenergic receptor, and a human histamine $H_1$ receptor; and b. binds to a human $\alpha_2$ adrenergic receptor with a binding affinity which is greater than 100-fold lower than the binding affinity with which the $\alpha_{1C}$ antagonist binds to such $\alpha_{1C}$ adrenergic receptor.

Another embodiment of the inventions provides for a method of inhibiting contraction of a prostate tissue in a subject which comprises administering to the subject an effective contraction-inhibiting amount of an $\alpha_{1C}$ antagonist which:

a. binds to a human $\alpha_{1C}$ adrenergic receptor with a binding affinity greater than 100-fold higher than the binding affinity with which the $\alpha_{1C}$ antagonist binds to a human $\alpha_{1A}$ adrenergic receptor, a human $\alpha_{1B}$ adrenergic receptor, and a human histamine $H_1$ receptor; and b. binds to a human $\alpha_2$ adrenergic receptor with a binding affinity which is greater than 100-fold lower than the binding affinity with which the $\alpha_{1C}$ antagonist binds to such $\alpha_{1C}$ adrenergic receptor.

Alternatively or incrementally, the $\alpha_{1C}$ antagonist used to practice the method of the invention additionally (a) binds to a human $\alpha_{1C}$ adrenergic receptor with a binding affinity greater than 300-fold higher than the binding affinity with which the $\alpha_{1C}$ antagonist binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than 300-fold lower than the binding affinity with which the $\alpha_{1C}$ antagonist binds to such $\alpha_{1C}$ adrenergic receptor.

Desirably, the $\alpha_{1C}$ antagonist used to practice the method of the invention additional binds to a calcium channel with a binding affinity which is greater than ten-fold lower than the binding affinity with which the $\alpha_{1C}$ antagonist binds to the $\alpha_{1C}$ adrenergic receptor.

In one embodiment, the $\alpha_{1C}$ antagonist used to practice the method of the invention additionally binds to a calcium channel with a binding affinity which is greater than 20-fold lower than the binding affinity with which the $\alpha_{1C}$ antagonist binds to the $\alpha_{1C}$ adrenergic receptor.

In a more preferred embodiment, the $\alpha_{1C}$ antagonist used to practice the method of the invention additionally binds to a calcium channel with a binding affinity which is greater than 50-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to a calcium channel with a binding affinity which is greater than 100-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to a calcium channel with a binding affinity which is greater than 300-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to a human dopamine $D_2$ or human histamine $H_2$ receptor with a binding affinity which is greater than ten-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to a human dopamine $D_2$ or human histamine $H_2$ receptor with a binding affinity which is greater than 20-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to a human dopamine $D_2$ or human histamine $H_2$ receptor with a binding affinity which is greater than 50-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to a human dopamine $D_2$ or human histamine $H_2$ receptor with a binding affinity which is greater than 100-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to a human dopamine $D_2$ or human histamine $H_2$ receptor with a binding affinity which is greater than 300-fold lower than the binding affinity with which the $\alpha_{1C}$ antagonist binds to the $\alpha_{1C}$ adrenergic receptor.

Desirably, the $\alpha_{1C}$ antagonist used to practice the method of the invention additionally binds to any serotonin receptor with a binding affinity which is greater than ten-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to any serotonin receptor with a binding affinity which is greater than 20-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to any serotonin receptor with a binding affinity which is greater than 50-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to any serotonin receptor with a binding affinity which is greater than 100-fold lower than the binding affinity with which the $\alpha_{1C}$ antagonist binds to the $\alpha_{1C}$ adrenergic receptor.

Alternatively or incrementally, the aic antagonist used to practice the method of the invention additionally binds to any serotonin receptor with a binding affinity which is greater than 300-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to a dopamine $D_3$, $D_4$, or $D_5$ receptor with a binding affinity which is greater than ten-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to a dopamine $D_3$, $D_4$, or $D_5$ receptor with a binding affinity which is greater than 20-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to a dopamine $D_3$, $D_4$, or $D_5$ receptor with a binding affinity which is greater than 50-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to a dopamine $D_3$, $D_4$, or $D_5$ receptor with a binding affinity which is greater than 100-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally binds to a dopamine $D_3$, $D_4$, or $D_5$ receptor with a binding affinity which is greater than 300-fold lower than the binding affinity with which the $\alpha_{1C}$ antagonist binds to the $\alpha_{1C}$ adrenergic receptor.

Alternatively or incrementally, the $\alpha_{1C}$ antagonist used to practice the method of the invention additionally does not cause a fall in blood pressure at dosages effective to alleviate benign prostatic hyperplasia.

In a preferred embodiment, the $\alpha_{1C}$ antagonist used to practice the method of the invention additionally does not cause a fall in blood pressure in rats at a dosage of 10 micrograms of $\alpha_{1C}$ antagonist per kilogram per rat.

The invention provides for the use of a compound which:

a. binds to a human $\alpha_{1C}$ adrenergic receptor with a binding affinity greater than 100-fold higher than the binding affinity with which the $\alpha_{1C}$ antagonist binds to a human $\alpha_{1A}$ adrenergic receptor, a human $\alpha_{1B}$ adrenergic receptor, and a human histamine $H_1$ receptor; and b. binds to a human $\alpha_2$ adrenergic receptor with a binding affinity which is greater than 100-fold lower than the binding affinity with which the $\alpha_{1C}$ antagonist binds to such $\alpha_{1C}$ adrenergic receptor in the preparation of a medicament for treating begin prostatic hyperplasia or inhibiting contraction of a prostate tissue.

In a preferred embodiment of the invention provides for a drug which is useful for treating benign prostatic hyperplasia or inhibiting contraction of a prostate tissue, the effective ingredient of the drug being an $\alpha_{1C}$ antagonist which:

a. binds to a human $\alpha_{1C}$ adrenergic receptor with a binding affinity greater than 100-fold higher than the binding affinity with which the $\alpha_{1C}$ antagonist binds to a human $\alpha_{1A}$ adrenergic receptor, a human $\alpha_{1B}$ adrenergic receptor, and a human histamine $H_1$ receptor; and b. binds to a human $\alpha_2$ adrenergic receptor with a binding affinity which is greater than 100-fold lower than the binding affinity with which the $\alpha_{1C}$ antagonist binds to such $\alpha_{1C}$ adrenergic receptor.

The present invention provides a method of treating benign prostatic hyperplasia in a subject which comprises administering to the subject a therapeutically effective amount of a compound which (a) binds to a human $\alpha_{1C}$ adrenergic receptor with a binding affinity greater than ten-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than ten-fold lower than the binding affinity with which the compound binds to such $\alpha_{1C}$ adrenergic receptor.

Ten-fold selectivity differences are a minimum, but one skilled in the art will appreciate that compounds can be found that collectively have almost infinitely variable selectivity profiles. Compounds collectively having all possible combinations of selectivities are intended within the scope of this invention, provided that each of these compounds has at least a ten-fold greater selectivity for the $\alpha_{1C}$ receptor over the $\alpha_{1A}$, $\alpha_{1B}$, $\alpha_2$ and $H_2$ receptors. For example, compounds useful in the methods of this invention can have at least a 10, 20, 30, 40, 50, 75, 100, 200, 300 or greater fold selectivity for binding to the $\alpha_{1C}$ receptor over binding to the $\alpha_{1A}$, $\alpha_{1B}$, $\alpha_2$ and $H_2$ receptors. The compounds useful in the methods of this invention can also have selectivity for the $\alpha_{1C}$ receptor over the $\alpha_{1A}$, $\alpha_{1B}$, $\alpha_2$ and $H_2$ receptors, such selectivity having a number-fold between these exemplary integers. Furthermore, these compounds can additionally have selectivity within the ranges described above for binding to the $\alpha_{1C}$ receptor over binding to (1) a calcium channel; and/or (2) a $D_2$ or H2 receptor; and/or (3) any serotonin receptor; and/or (4) a dopamine $D_3$, $D_4$ or $D_5$ receptor.

In the preferred embodiment, the compound (a) binds to a human $\alpha_{1C}$ adrenergic receptor with a binding affinity greater than 20-, 50-, 100- or 300-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than 20-, 50-, 100- or 300-fold lower than the binding affinity with which the compound binds to such $\alpha_{1C}$ adrenergic receptor.

Desirably, the compound used to practice the method of the invention additionally binds to a calcium channel with a binding affinity which is greater than ten-fold lower than the binding affinity with which the compound binds to the $\alpha_{1C}$ adrenergic receptor.

In the preferred embodiment, the compound binds to a calcium channel with a binding affinity which is greater than 20-, 50-, 100- or 300-fold lower than the binding affinity with which the compound binds to the $\alpha_{1C}$ adrenergic receptor.

Alternatively or incrementally, the compound used to practice the method of the invention additionally binds to a human dopamine $D_2$ receptor or human $H_2$ receptor with a binding affinity which is greater than ten-fold lower than the binding affinity with which the compound binds to the $\alpha_{1C}$ adrenergic receptor.

In the preferred embodiment, the compound binds to a human dopamine $D_2$ or human $H_2$ receptor with a binding affinity which is greater than 20-, 50-, 100- or 300-fold lower than the binding affinity with which the compound binds to the $\alpha_{1C}$ adrenergic receptor.

Alternatively or incrementally, the compound used to practice the method of the invention additionally binds to any serotonin receptor with a binding affinity which is greater than ten-fold lower than the binding affinity with which the compound binds to the $\alpha_{1C}$ adrenergic receptor.

In the preferred embodiment, the compound binds to any serotonin receptor with a binding affinity which is greater than 20-, 50-, 100- or 300-fold lower than the binding affinity with which the compound binds to the $\alpha_{1C}$ adrenergic receptor.

Alternatively of incrementally, the compound used to practice the method of the invention also binds to a human dopamine $D_3$, $D_4$ or $D_5$ receptor with a binding affinity which is greater than ten-fold lower than the binding affinity with which the compound binds to the $\alpha_{1C}$ adrenergic receptor.

In the preferred embodiment, the compound binds to a dopamine $D_3$, $D_4$, or $D_5$ receptor with a binding affinity which is greater than 20-, 50-, 100- or 300-fold lower than the binding affinity with which the compound binds to the $\alpha_{1C}$ adrenergic receptor Alternatively or incrementally, the compound used to practice the method of the invention also does not cause orthostatic fall in blood pressure at a dosage effective to alleviate benign prostatic hyperplasia or inhibiting contraction of prostate tissue.

In one embodiment, the compound used to practice the method of the invention also does not cause orthostatic fall in blood pressure in rats at a dosage 10 ug/kg.

A number of compounds have been identified or synthesized which are useful in the practice of the invention. For example, the compound has the structure:

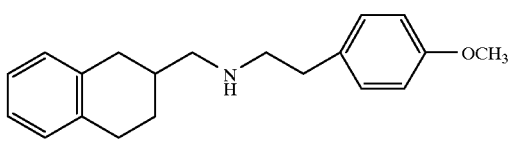

In another example, the compound has the structure:

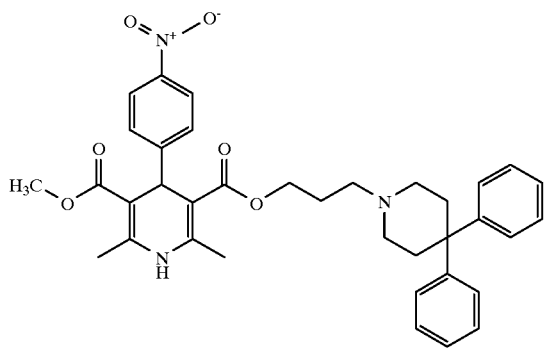

In still another example, the compound has the structure:

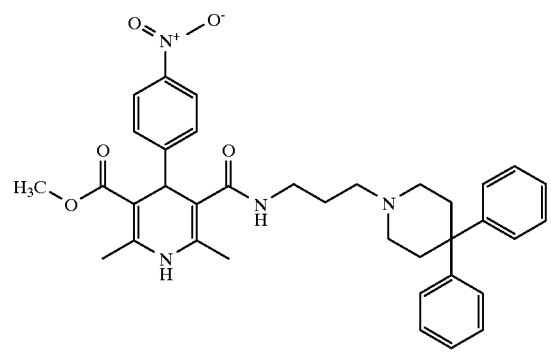

In an additional example, the compound has the structure:

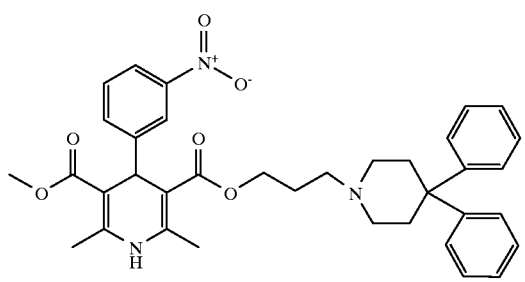

Included within the scope of the method of treating BPH in accordance with the invention are the use of both R and S enantiomers of the compounds described which possess stereogenic centers, as well as the use of pharmaceutically acceptable salts and complexes thereof.

The invention also provides a method of inhibiting contraction of prostate tissue which comprises contacting the prostate tissue with an effective contraction-inhibiting amount of a compound which (a) binds to a human $\alpha_{1C}$ adrenergic receptor with a binding affinity greater than ten-fold higher than the binding affinity with which the compound binds to a human $\alpha_{1A}$ adrenergic receptor, a human $\alpha_{1B}$ adrenergic receptor, and a human histamine $H_1$ receptor, and (b) binds to a human $\alpha_2$ adrenergic receptor with a binding affinity which is greater than ten-fold lower than the binding affinity with which the compound binds to such $\alpha_{1C}$ adrenergic receptor.

In the preferred embodiment, the compound (a) binds to a human $\alpha_{1C}$ adrenergic receptor with a binding affinity greater than 20-, 50-, 100- or 300-fold higher than the binding affinity with which the compound binds to a human $\alpha_{1A}$ adrenergic receptor, a human $\alpha_{1B}$ adrenergic receptor, and a human $H_1$ receptor, and (b) binds to a human $\alpha_2$ adrenergic receptor with a binding affinity which is greater than 20-, 50-, 100- or 300-fold lower than the binding affinity with which the compound binds to such $\alpha_{1C}$ adrenergic receptor.

The activity of compounds at the different human receptors was determined in vitro using cultured cell lines that selectively express the receptor of interest. These cell lines were prepared by transfecting the cloned cDNA or cloned genomic DNA or constructs containing both genomic DNA and cDNA encoding the human α-adrenergic, serotonin, histamine, and dopamine receptors as further described in detail in Example 10 hereinbelow.

In connection with this invention, a number of cloned human receptors discussed herein, either as plasmids or as stably transfected cell lines, have been made pursuant to, and in satisfaction of, the Budapest Treaty on the International Recognition of the Deposit of Microorganisms for the Purpose of Patent Procedure, and are made with the American Type Culture Collection, 12301 Parklawn Drive, Rockville, Md. 20852. Specifically, these deposits have been accorded ATCC Accession Numbers as follows:

| Designation | ATCC Accession No. | Date |
|---|---|---|
| L-$\alpha_{1A}$ | CRL 11138 | September 25, 1992 |
| L-$\alpha_{1B}$ | CRL 11139 | September 25, 1992 |
| L-$\alpha_{1C}$ | CRL 11140 | September 25, 1992 |
| L-$\alpha_{2A}$ | CRL 11180 | November 6, 1992 |
| L-NGC-$\alpha_{2B}$ | CRL 10275 | October 25, 1989 |
| L-$\alpha_{2C}$ | CRL 11181 | November 6, 1992 |
| pcEXV-$H_1$ | 75346 | November 6, 1992 |
| pcEXV-$H_2$ | 75345 | November 6, 1992 |
| pcEXV-$D_2$ | 75344 | November 6, 1992 |

The data shown in the accompanying Tables indicate that the $\alpha_{1C}$-specific receptor antagonists which satisfy the criteria as defined herein have significant efficacy in the inhibition of contraction of human prostate tissue. This in vitro property is recognized in the art as correlating with efficacy in treating benign prostatic hyperplasia in vivo.

The present invention therefore provides a method of treating benign prostatic hyperplasia, which comprises administering a quantity of any of the $\alpha_{1C}$ receptor antagonists defined as herein in a quantity effective against BPH. The drug may be administered to a patient afflicted with benign prostatic hyperplasia by any conventional route of administration, including, but not limited to, intravenous, intramuscular, oral, subcutaneous, intratumoral, intradermal, and parenteral. The quantity effective against BPH is between 0.001 mg and 10.0 mg per kg of subject body weight.

The method of treating BPH disclosed in the present invention may also be carried out using a pharmaceutical composition comprising any of the $\alpha_{1C}$ receptor antagonists as defined herein and a pharmaceutically acceptable carrier. The composition may contain between 0.05 mg and 500 mg of an $\alpha_{1C}$ receptor antagonist, and may be constituted into any form suitable for the mode of administration selected. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The drug may otherwise be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

Optimal dosages to be administered may be readily determined by those skilled in the art, and will vary with the particular $\alpha_{1C}$ receptor antagonist in use, the strength of the preparation, the mode of administration, and the advancement of the disease condition. Additional factors depending on the particular patient being treated will result in a need to adjust dosages, including patient age, weight, diet, and time of administration.

The term "therapeutically effective amount" as used herein means that amount of active agonist or pharmaceutical agent that elicits the biological or medicinal response in a tissue, system, animal or human that is being sought by a researcher, veterinarian, medical doctor or other clinician, which includes alleviation of the symptoms of the disease being treated.

The term "subject," as used herein refers to an animal, preferably a mammal, most preferably a human, who has been the object of treatment, observation or experiment.

The following Experimental Details are set forth to aid in an understanding of the invention, and are not intended, and should not be construed, to limit in any way the invention set forth in the claims which follow thereafter.

EXPERIMENTAL DETAILS

Prazosin, 5-methylurapidil, and S-niguldipine were obtained from Research Biochemicals, Inc. A30360 (4-fluoro-4-(8-fluoro-1,3,4,5-tetrahydro-2H-pyrido[4,3-b]indol-2-yl)butyrophenone hydrochloride) was obtained from Aldrich Chemical Co. Other compounds were prepared according to the examples which follow.

EXAMPLE 1

Synthesis of Terazosin Hydrochloride
N-(2-Furoyl)piperazine

This compound and its preparation has been described in Great Britain Patents 1,390,014 and 1,390,015. Piperazine hexahydrate (194 g, 1 mole) was dissolved in 250 ml $H_2O$. The solution was acidified to pH 4.5 with 6 N HCl. Furoyl chloride (130.5 g, 1 mole, Aldrich) was added along with 10% NaOH solution at such a rate that the pH was maintained at 4.5. After 1 hour, the solution was made basic (pH=8.5) with NaOH solution. The reaction mixture was continuously extracted with chloroform for 36 hours. The $CHCl_3$ extract was dried over $MgSO_4$, and filtered. Distillation gave 108.2 g product (60%), b.p. 132°–138° C../0.6 mm Hg, m.p. 69°–70° C..
N-(Tetrahydro-2-furoyl)piperazine The furoylpiperazine of Example 1 was converted to the hydrobromide salt (m.p. 173°–175° C..). This salt (39.0 g) in 250 ml methyl alcohol and 9.0 g Raney nickel was hydrogenated at 3 atm. After uptake of $H_2$ ceased, the catalyst was filtered, the solvent concentrated, and the residue crystallized from isopropyl alcohol to give 35.2 g. tetrahydrofuroylpiperazine HBr, m.p. 152°–156° C.. This was suspended in 20 ml $H_2O$. Then 10.5 g 50%, NaOH solution was added slowly followed by 2.0 g solid $Na_2CO_3$. This was extracted with 4×100 ml portions of warm $CHCl_3$. The $CHCl_3$ extractions were distilled to give 22.5 g tetrahydrofurolylpiperazine, b.p. 120°–125° C../0.2 mm Hg.
2-[4-(Tetrahydro-2-furoyl)piperazinyl]-4-amino-6,7-dimethoxyquinazoline hydrochloride To 7.00 g 2-chloro-4-amino-6,7-dimethoxyquinazoline (Lancaster Synthesis) in 50 ml methoxyethanol was added 10.8 g, tetrahydrofurolylpiperazine, and the mixture refluxed 3 hours. The clear solution was concentrated and an aqueous solution of potassium bicarbonate was added. The resultant solid that formed was filtered and washed with water. It was then added to methanol and the resulting suspension was acidified with a solution of hydrogen chloride in isopropyl alcohol. The resulting solution was concentrated and the residue crystallized from isopropyl alcohol giving 8.12 g. of product, m.p. 278°–279° C..

EXAMPLE 2

Preparation of Indoramin
4-Benzamido-1-[2-(3-indolyl)ethylpyridinium Bromide

A solution of 4-benzamidopyridine (1.98 g) and 3-(2-bromoethyl)indole (2.24 g) in EtOH (15 ml) was refluxed for 2 hours, and the crystallized product (3.13 g, mp 264–266° C..) was collected by filtration from the hot reaction mixture. Recyrstallization gave the hydrate.

3-[2-4-Benzamidopiperid-1-yl]ethyl]indole (Indoramin)

4-Benzamido-1-[2-(3-indolyl)ethyl]pyridinium bromide (3.0g) in 91% EtOH (300 ml) containing $Et_3N$ (0.8 g) was hydrogenated in the presence of freshly prepared W-7 Raney Ni catalyst (ca. 3 g) at 28.12 kg/cm$^2$ and 50° for 4 hours. After filtering off the catalyst, the filtrate was evaporated and the residue was shaken with $CHCl_3$ and 2 N NaOH. The resulting insoluble material (1.61 g, mp 203–206° C..) was collected and dried. Recrystallization from EtOH gave the product (1.34 g), as colorless needles.

EXAMPLE 3

Preparation of 1-(3-benzoylpropyl)-4-benzamidopiperidine

A mixture of 4-chlorobutyrophenone (447 mg, 2.45 mmol), 4-benzamidopiperidine (500 mg, 2.45 mmol) and $K_2CO_3$ (338 mg, 2.45 mmol) was heated up in boiling water bath for 1 hour. The reaction mixture was portioned between water and $CHCl_3$. The organic layer was separated and dried over $Na_2SO_4$. After filtration and removal of solvent, the residue was purified by chromatography ($SiO_2$, MeOH:$CHCl_3$, 5:95). Recrystallization from AcOEt/hexane gave a white powder (78 mg, 8.2%). mp 143–144° C.; $^1H$ NMR ($CD_3OD$, 400 MHz) δ 1.65 (dq, $J_1$=3.16 Hz, $J_2$=11.9 Hz, 2H), 1.90–2.00 (m, 4H), 2.18 (t, J=11.9 Hz, 2H), 2.48 (m, 2H), 3.00–3.10 (m, 4H), 3.88 (m, 1H), 7.40–8.00 (m, 10H); Mass spectrum (M+1)$^+$ at m/z 351.

EXAMPLE 4

Preparation of 1-[3-(4-chlorobenzoyl)propyl]-4-benzamidopiperidine

A mixture of 3-(4-chlorobenzol)propyl bromide (640 mg, 2.45 mmol), 4-benzamidopiperidine (500 mg, 2.45 mmol) and $K_2CO_3$ (1.01 g, 7.34 mmol) in 50 ml of acetone was heated up to refluxing condition for 48 hours. The solid was removed by filtration. Concentration of filtrate in vacuo gave a yellowish solid, which was purified by chromatography ($SiO_2$, MeOH:$CHCl_3$, 5:95). 320 mg (33.9%) of white powder was obtained $^1H$ NMR ($CDCl_3$, 300 mHz) δ 1.46 (dq, $J_1$=1.0 Hz, $J_2$=8.4 Hz, 2H), 1.90–2.10 (m, 4H), 2.16 (m, 2H), 2.43 (t, J=6.9 Hz, 2H), 2.80–2.90 (m, 2H), 2.97 (t, J=6.9 Hz, 2H), 3.97 (m, 1H), 5.92 (d, J=7.8 Hz, 1H, N-H), 7.40–8.00 (m, 9H); Product was converted to HCl salt and recrystallized with MeOH/$Et_2O$, mp 243–244° C..; Calcd for $C_{22}H_{25}ClN_2O_2 \cdot HCl \cdot H_2O$: C 60.15, H 6.37, N 6.37; Found: C 60.18, H 6.34, N6.29.

EXAMPLE 5

Preparation of SKF-104856
1-[(4-Chlorophenyl)thio}-2-propanone

Chloroacetone (32.3 g, 0.347 mol) was added to a mixture of 4-chlorothiophenol (50 g, 0.347 mmol) and sodium hydroxide (14 g, 0.347 mol) in water (400 ml) and the mixture was stirred at 25° C.. for 1 hour. The mixture was extracted with ethyl ether and the organic phase was washed with water, dried with magnesium sulfate and concentrated to give 69 g (99%) of 1-[(4-chlorophenyl)thio]-2-propanone.

5-Chloro-3-methylbenzo(b)thiophene

1-[(4-Chlorophenyl)thio}-2-propanone (50 g, 0.25 mol) was added to polyphosphoric acid (300 g) and the mixture was stirred as the temperature was gradually raised to 120° C.. as an exotherm started. The mixture was stirred at 130° C.. for 1 hour, diluted with water, extracted with ethyl ether and the organic phase was dried and concentrated. The residue was stirred in methanol (200 ml), filtered and the filtrate concentrated to give 17.5 g (40%) of 5-chloro-3-methylbenzo(b)thiophene: bp 120° C.. (0.6 mm Hg).

Ethyl 5-chloro-3-methylbenzo(b)thiophene-2-carboxylate n-Butyllithium in hexane (2.6 M, 2.3 ml) was added to a solution of 5-chloro-3-methylbenzo(b)thiophene (1,0 g, 6 mmol) in ethyl ether (20 ml) stirred at 0° C.. under argon. The mixture was stirred for 30 minutes and transferred slowly under argon pressure to a stirred solution of ethyl chloroformate (0.63 g, 6 mmol) in ethyl ether (20 ml). The mixture was stirred at 0° C.. for 30 minutes and at 25° C.. for 1.5 hours. The mixture was treated with water and the organic phase was dried, concentrated and triturated with hexane to give 1.0 g (67w) of ethyl 5-chloro-3-methylbenzo (b)thiophene-2-carboxylate: mp 92.5–94° C..

Ethyl 3-bromomethyl-5-chlorobenzo(b)thiophene-2-carboxylate

A mixture of ethyl 5-chloro-3-methylbenzo(b)thiophene-2-carboxylate (9.0 g, 0.035 mol), N-bromosuccinimide (6.53 g, 0.037 mol) and benzoyl peroxide (130 mg) in carbon tetrachloride (150 ml) was refluxed and illuminated with sunlamp for 2 hours. The resulting suspension was cooled, filtered and the filter cake was triturated with methanol to give 9.9 g, (85%) of the methanol-insoluble ethyl 3-bromomethyl-5-chlorobenzo(b)thiophene-2-carboxylate: mp 148–150° C..

Ethyl 5-Chloro-3-[N-(2,2-dimethoxyethyl)-N-methyl (aminomethyl)]benzo(b)thiophene-2-carboxylate A mixture of ethyl 3-bromomethyl-5-chlorobenzo(b) thiophene-2-carboxylate (11 g, 0.033 mol), methylaminoacetaldehyde dimethyl acetal (4.76 g, 0.04 mol) and potassium carbonate (11.4 g, 0.8 mol) in dry acetone (200 ml) was stirred for 48 hours, filtered and the filtrate concentrated to give 11.8 g, (96%) of ethyl 5-chloro-3-(N-2,2-dimethoxyethyl)-N-methyl(aminomethyl)benzol(b) thiophene-2-carboxylate.

Ethyl 7-chloro-3,4-dihydro-4-methylthieno[4,3,2-ef][3]benzazepine-2-carboxylate

Ethyl 5-chloro-3-[N-(2,2-dimethoxyethyl)-N-methyl (aminomethyl)]benzo[b]thiophene-2-carboxylate (3.0 g, 8.1 mmol) was added in portions to trifluoromethanesulfonic acid (10 ml) stirred at 0° C.. under argon. The mixture was stirred at 25° C.. for 45 minutes and diluted with water. The mixture was basified with aqueous sodium hydroxide and extracted with ethyl ether to give ethyl 7-chloro-3,4-dihydro-4-methylthieno-[4,3,2-ef][3]benzazepine-2-carboxylate.

Ethyl 7-chloro-3,4,5,6-tetrahydro-4-methylthieno[4,3,2-ef][3]benzazepine-2-carboxylate Diborane in tetrahydrofuaran (1 M, 40 ml) was added to a solution of ethyl 7-chloro-3,4-dihydro-4-methylthieno-[4,3,2-ef][3]benzazepine-2-carboxylate (2.8 g) in tetrahydrofuran (30 ml) stirred at 0° C.. The mixture was refluxed for 3 hours and stirred at 25 C. for 18 hours, cooled, treated with methanol (50 ml), refluxed for 18 hours and concentrated. The residue was triturated with ethyl ether-hexane (3:1) to give 1.6 g (84) of ethyl 7-chloro-3,4,5,6-tetrahydro-4-methylthieno[4,3,2-ef][3]benzazepine-2-carboxylate: mp 138–140° C.. The free base was treated with hydrogen chloride to give ethyl 7-chloro-3,4,5,6-tetrahydro-4-methylthieno[4,3,2-ef][3]benzazepine-2-carboxylate hydrochloride: mp 240° C..

7-Chloro-3,4,5,6-tetrahydro-4-methylthieno[4,3,2-ef][3]benzazepine-2-methanol

A solution of ethyl 7-chloro-3,4,5,6-tetrahydro-4-methylthieno[4.3.2-ef][3]benzazepine-2-carboxylate (4.0 g, 12.9 mmol), in ethyl ether (48 ml) was treated with lithium aluminum hydride (0.53 g, 14 mmol). The mixture was stirred for 1.5 hours, cooled and treated carefully with water (2.0 ml), 10% sodium hydroxide (1.0 ml) and water (2.0 ml). The resulting mixture was filtered and the solvent evaporated to give 1.9 g (57%) of 7-chloro-3,4,5,6-tetrahydro-4-methylthieno[4,3,2-ef][3]benzazepine-2-methanol: mp 184–185° C..

7-Chloro-3,4,5,6-tetrahydro-4-methylthieno-4,3,2-ef][3]benzazepine-2-carboxaldehyde A solution of 7-chloro-3,4,5,6-tetrahydro-4-methylthieno[4,3,2-ef][3]benzazepine-2-methanol (1.6 g, 6 mmol) in dichloromethane (150 ml) was stirred under argon with activated manganese dioxide (8.3 g) for 2 hours. The mixture was filtered through Celite™ and the filtrate was dried with magnesium sulfate and concentrated to give a 63% yield of 7-chloro-3,4,5,6-tetrahydro-4-methylthieno[4,3,2-ef[[3]benzazepine-2-carboxaldehyde.

7-Chloro-2-ethenyl-3,4,5,6-tetrahdyro-4-methylthieno-[4,3,2-ef][3]benzazepine (SKF-104856)

Sodium hydride (60 %o dispersion in mineral oil. 3.8 mmol) was added to a stirred solution of methyltriphenylphosphonium bromide (1.35 g, 3.8 mmol) in dry tetrahydrofuran (30 ml) and stirred for 15 minutes. The mixture was treated with a solution of 7-chloro-3,4,5,6-tetrahydro-4-methylthieno[4,3,2-ef][3]-benzazepine-2-carboxaldehyde, prepared as in Example 3, (0.5 g, 1.9 mmol) in dimethyl-formamide (4 ml), stirred at 25° C.. for 16 hours, quenched with ice and extracted with ethyl acetate. The organic phase was washed, dried and concentrated and the residue was chromatographed on silica gel eluted with a gradient of methylene chloride to methanol-methylene chloride (3.5:96.5). The product was treated with hydrogen chloride to give 0.2 g (35%) of 7-chloro-2-ethenyl-3,4,5,6-tetrahydro-4-methylthieno-[4,3,2-ef][3]benzazepine hydrochloride: mp 234–236° C..

EXAMPLE 6

2-Hydroxymethyl-1,2,3,4-tetrahydronaphthalene

A solution of 1,2,3,4-tetrahydro-2-naphthoic acid (2.50 g, 14.2 mmol) in 100 ml THF was treated with LiAlH$_4$ (681 mg, 17.04 mmol) and the reaction mixture was heated at reflux for 5 hours. The suspension was cooled to 0° C.. and quenched by addition of solid Na$_2$SO$_4$.■10H$_2$O. The mixture was stirred at room temperature for 4 hours. The solid was removed by filtration. Concentration of filtrate in vacuo gave a yellowish oil (2.28 g, 98.8%); $^1$H NMR (CDCl$_3$, 300 MHz) δ 1.43 (m, 1H), 2.00 (m, 2H) 2.51 (dd, J$_1$=16.5 Hz, J$_2$=10.8 Hz, 1H), 2.85 (m, 3H), 3.65 (dd, J$_1$=6.3 Hz, J$_2$=1.2 Hz, 2H), 7.09 (s, 4H).

2-Bromomethyl-1,2,3,4-tetrahydronaphthalene

A solution of 2-hydroxymethyl-1,2,3,4-tetrahydronaphthalene (2.28 g, 14.0 mmol) in 100 ml of CH$_2$Cl$_2$ was treated with PBr$_3$ (1.28 g, 4.73 mmol) at 0° C.. The mixture was stirred at room temperature for 72 hours then poured onto 100 g of ice. The organic layer was isolated, washed with 10% K$_2$CO$_4$ aqueous solution, H$_2$O, sat'd brine, and then dried over Na$_2$SO$_4$. After filtration and removal of solvent, the residue was purified by chromatography (SiO$_2$, EtOAc:hexane, 1:10) to give a colorless oil (1.33 g, 41.6%); $^1$H NMR (CDCl$_3$, 300 MHz) δ 1.55 (m, 1H), 2.11 (m, 1H), 2.11 (m, 2H), 2.58 (dd, J$_1$=16.2 Hz, J$_2$=10.2 Hz, 1H), 2.80–3.10 (m, 3H), 3.45 (d, J=6.3 Hz, 2H), 7.10 (m, 4H).

2-[(4-Methoxyphenethyl)aminomethyl]-1,2,3,4-tetrahydronaphthalene (Compound 11)

A solution of 2-bromomethyl-1,2,3,4-tetrahydronaphthalene (1.33 g, 5.91 mmol) and 4-methoxyphenethylamine (1.79 g, 11.8 mmol) in 50 ml of EtOH was refluxed for 48 hours. After removal of EtOH in vacuo, the residue was dissolved in 100 ml of CHCl$_3$, washed with 10% K$_2$CO$_3$, H$_2$O, sat'd brine, and then dried over Na$_2$SO$_4$. Filtration followed by evaporation of solvent gave a yellow oil, which was purified by chromatography (SiO$_2$, MeOH:CHCl$_3$, 5:95) to a give a yellowish oil (1.03 g, 58.9%). The product was converted to HCl salt, crystallization with MeOH/Et$_2$O gave a white powder. mp 274–275° C..; Calcd for C$_{20}$H$_{25}$NO.HCl: C 72.37, H 7.91, N 4.22; Found C 72.40, H 7.76, N 4.13.

EXAMPLE 7

4,4-Diphenylpiperidine hydrochloride

A mixture of 4-piperidone monohydrate hydrochloride (15.0 g, 97.6 mmol, 1.00 equiv, Aldrich) and AlCl$_3$ (130 g, 976 mmol, 10.0 equiv) in anhydrous benzene (600 mL) was stirred at reflux for 4 hours. Ice (300 g) and water (50 mL) were added, the mixture was filtered, and the solid was washed with toluene and dried to afford 19.2 g (72%) of off-white solid, which was pure by $^1$H NMR. Recrystallization from ethanol gave the analytically pure sample: m.p. 300–301° C..; $^1$H NMR (300 MHz, CD$_3$OD) δ 2.65 (m, 4 H), 3.18 (m, 4 H), 7.18 (m, 2 H), 7.30 (m, 8 H); Anal. Calcd. for C$_{17}$H$_{19}$N.HCl: C, 74.57; H. 7.36; N, 5.12. Found: C, 74.32; H, 7.34; N, 5.02. The free base was generated by addition of the above salt to dilute aqueous sodium hydroxide and extraction with CH$_2$Cl$_2$. The organic phase was dried over MgSO$_4$ and concentrated to give a light brown solid: IR (neat) 2942.8, 1494.5, 1445.9 cm$^{-1}$; CIMS (NH$_3$) m/e 238 (M+1)$^+$.

3-(4,4-Diphenylpiperidin-1-yl)propionitrile

To a suspension of 4,4-diphenylpiperidine hydrochloride (195 mg, 0.712 mmol, 1.0 equiv) in ETOh (1.5 mL) was added triethylamine (0.25 mL, 1.83 mmol, 2.6 equiv) followed by acrylonitrile (0.13 mL, 2.01 mmol, 2.8 equiv). The resulting solution was stirred at room temperature under argon for 15 minutes and then concentrated. Water was added, and the mixture was extracted three times with EtOAc. The combined organic extracts were dried over MgSO$_4$ and concentrated to give 170 mg (87%) of tan solid, which was used for the next reaction without purification. m.p. 95–96° C..; $^1$H NMR (300 MHz, CDCl$_3$) δ 2.37 (m, 2H), 2,46 (m, 4H), 2.52 (m, 6H), 7.12 (m, 2H), 7.23 (m, 8H); $^{13}$C NMR (75 MHz, CDCl$_3$) δ 16.65, 36.71. 45.08, 50.78, 54.13, 119.70, 126.48, 127.78, 129.11, 147.87; IR (neat) 2944.4, 2821.0, 1495.5, 1445.9 cm$^{-1}$.

1-(3-Aminopropyl)-4,4-diphenylpiperidine

To a stirred solution of 3-(4,4-diphenylpiperidine-1-yl) propionitrile (2.00 g, 6.89 mmol, 1.0 equiv) in anhydrous THF (20 mL) under argon was added a solution of BH$_3$ in THF (1.0 M, 24.1 mL, 24 mmol, 3.5 equiv) at room temperature. The mixture was refluxed for 4.5 hours and then cooled to room temperature. Aqueous HCl (6 N, 50 mL) was added and stirring was continued for 1 hour. The mixture was basified to pH 9 by addition of 6 N aq. NaOH, extracted 3 times with CH$_2$Cl$_2$, dried over MgSO$_4$ and concentrated. The residue was purified by flash chromatography (SiO$_2$, EtOAc-MeOH, 9:1, followed by EtOAc-MeOH-isopropylamine (60:10:1), followed by EtOAc-MeOH-isopropylamine (40:10:2) to give 1.35 g (66%) of tan solid: m.p. 98–99° C..; $^1$H NMR (300 MHz, CDCl$_3$) δ 1.64 (tt, J=7.7 Hz, 2H), 2.33 (br t, J=7.2 Hz, 2H), 2.50 (m, 8H), 2.76 (br t, J=6.5 Hz, 2H), 3.06 (br s, 2H), 7.13 (m, 2H), 7.26 (m, 8H); $^{13}$C NMR (75 MHz, CDCl$_3$) δ 29.79, 36.80, 41.41, 45.24, 51.25, 57.41, 126.30, 127.77, 128.97, 148.11; IR (neat) 3361.5 cm$^{-1}$; CIMS (NH$_3$) m/e 295 (M+1)$^+$.

Acetoacetic acid N-13-(4,4-diphenylpiperidin-1-yl)propyl] amide

Diketene (0.44 mL, 5.68 mmol, 1.3 equiv, Aldrich) was added at room temperature to a stirred solution of 1-(3-aminopropyl)-4,4-diphenylpiperidine (1.288 g, 4.37 mmol, 1.0 equiv) in anhydrous toluene (15 mL) under argon, and stirring was continued for 48 hours. The mixture was concentrated to give 1.294 g (78%) of white solid, which was used for the next reaction without purification: $^1$H NMR (300 MHz, CDCl$_3$) δ 1.70 (tt, J=6.4, 6.4 Hz, 2H), 2.23 (s, 3H), 2.44 (br t, J=6.5 Hz), 2.49–2.67 (m, 8H), 3.32 (br t, J=5.8 Hz), 3.36 (s, 2H), 7.16 (m, 2H), 7.27 (m, 8H).

2,6-Dimethyl-4-(4-nitrophenyl)-1,4-dihydropyridine-3,5-dicarboxylic acid N-[3-(4,4-diphenylpiperidin-1-yl)propyl] amide methyl ester A solution of acetoacetic acid N-[3-(4,4-diphenylpiperidin-1-yl)propyl]amide (365 mg, 0.964 mmol, 1.0 equiv), methyl 3-aminocrotonate (138 mg, 1.20 mmol, 1.2 equiv, Aldrich), and 4-nitrobenzaldehyde (181 mg, 1.20 mmol, 1.2 equiv, Aldrich) in isopropanol was refluxed under argon for 60 hours. The mixture was cooled to room temperature and concentrated, and the residue was diluted with CH$_2$Cl$_2$, washed with water, dried over MgSO$_4$, and concentrated. The residue was purified by flash chromatography (SiO$_2$, EtOAc, followed by EtOAc-MeOH, 19:1 and 9:1) to give 147.8 mg (25%) of yellow solid: $^1$H NMR (300 MHz, CDCl$_3$) δ 1.55 (m, 2H), 2.14 (s, 3H), 2.15–2.50 (m, 10H), 2.32 (s, 3H), 3.20 (m, 1H), 3.37 (m, 1H), 3.54 (s, 3H), 5.00 (s, 3H), 5.48 (br s), 6.98 (br t, J=4.9 Hz, 1H), 7.14–7.30 (m, 10H), 7.39 (dm, J=8.7 Hz, 2H), 8.05 (dm, J=8.7 Hz, 2H); $^{13}$C NMR (75 MHz, CDCl$_3$) δ 18.74, 20.64, 25.61, 36.77, 40.20, 42.26, 45.03, 51.16, 51.61, 58.08, 100.65, 109.71, 124.35, 126.46, 127.61, 128.84, 129.06, 135.52, 146.96, 147.10, 154.55, 168.22, 168.70; IR (neat) 1680, 1610, 1515, 1340 cm$^{-1}$; MS (FAB) m/e 609 (M+H)$^+$.

2,6-Dimethyl-4-(4-nitrophenyl)-1,4-dihydropyridine-3,5-dicarboxylic acid N-[3-(4,4-diphenylpiperidin-1-yl)propyl] amide methyl ester hydrochloride hydrate (Compound 2)

To a solution of 2,6-dimethyl-4-(4-nitrophenyl)-1,4-dihydro-pyridine-3,5-dicarboxylic acid N-[3-(4,4-diphenylpiperidin-1-yl)propyl]amide methyl ester (147.8 mg, 0.243 mmol, 1.0 equiv) in EtOH (2 mL) was added a solution of HCl in ether (1.0 M, 0.24 mL, 0.24 mmol, 1.0 equiv). Addition of ethyl acetate (3 mL) followed by heating gave a clear solution. Slow cooling of this solution, followed by filtration gave 91 mg of yellow crystalline solid: m.p. 182–183° C..; Anal. Calcd. for C$_{36}$H$_{40}$N$_4$O$_5$.HCl.H$_2$O: C, 65.20, H, 6.54; N, 8.45. Found: C, 65.30; H, 6.28; N, 8.15.

EXAMPLE 8

3-(4,4-Diphenylpiperid-1-yl)-propanol 4,4-Diphenylpiperidine (40 g), 3-bromopropanol (24.7 g, Aldrich), powdered potassium carbonate (116.4 g) and approximately 1 g of potassium iodide (in 500 ml of a 1:1 mixture of dioxane and 1-butanol) were heated for about 48 hours under reflux and with vigorous stirring. After cooling, the mixture was filtered, and the filtrate was concentrated. The oily residue was taken up in ethyl acetate, and the solution was filtered again. Concentrating the filtrate to dryness yielded the product in the form of a yellowish, oily residue which slowly solidifies to a wax-like product (yield: 44.8 g). Hydrochloric acid in ether produced the hydrochloride (m.p.: 226° to 2270° C..), which was recrystallized from 2-propanol.

Acetoacetic acid 3-(4,4-diphenylpiperidin-1-yl)propyl ester 23.6 g of 3-(4,4-diphenylpiperid-1-yl)-propanol were dissolved in 100 ml of absolute toluene, and 16 ml of a 50% strength solution of diketene in acetone were added with stirring. After standing for several days at room temperature (monitored by thin layer chromatography), the mixture was concentrated, and the residue was dried under high vacuum. The pale yellow, viscous oil which remains was employed without further purification for the next stage.

2,6-Dimethyl-4-(4-nitrophenyl)-1,4-dihydropyridine-3,5-dicarboxy-ylic acid [3-(4,4-diphenylpiperidin-1-yl)propyl] ester methyl ester A solution of methyl 3-aminocrotonate (265 mg, 2.3 mmol, 1.0 equiv), 4-nitrobenzaldehyde (348 mg, 2.3 mmol, 1.0 equiv), and acetoacetic acid 3-[4,4-diphenylpiperidin-1-yl)propyl] ester (872 mg, 2.3 mmol, 1.0 equiv) in isopropanol was refluxed under argon with stirring for 68 hours. Cooling and removal of solvent gave a residue, which was purified by flash chromatography (SiO$_2$, EtOAc-hexane, 1:1 and 1:2, followed by EtOAc) to afford 717 mg (51%) of yellow solid: $^1$H NMR (300 MHz, CDCl$_3$) δ 1.73 (m, 2H), 2.22 (m, 2H), 2.30–2.51 (m, 8H), 2.34 (s, 3H), 2.35 (s, 3H), 3.63 (s, 3H), 4.05 (dt, J=2.1, 7.9 Hz, 2H), 5.06 (s, 1H), 5.73 (br s, 1H), 7.14 (m, 2H), 7.27 (m, 8H), 7.42 (dm, J=8.8 Hz, 2H), 8.06 (dm, J=8.8 Hz, 2H); $^{13}$C NMR (75 MHz, CDCl$_3$) δ 15.30, 19.65, 26.32, 36.11, 39.88, 44.60, 50.60, 51.12, 55.34, 62.66, 102.99, 107.55, 123.39, 125.67, 127.12, 128.33, 128.65, 144.80, 144.93, 146.36, 147.50, 154.78, 166.91, 167.43; IR (neat) 1698.0, 1684.7, 1517.5, 1345.7 cm$^{-1}$; CIMS (NH$_3$) 610 (M+1)$^+$, 553, 338.

2,6-Dimethyl-4-(4-nitrophenyl)-1,4-dihydropyridine-3,5-dicarboxylic acid [3-(4,4-diphenylpiperidin-1-yl)propyl] ester methyl ester hydrochloride (Compound 8)

To a solution of 2,6-dimethyl-4-(4-nitrophenyl)-1,4-dihydro-pyridine-3,5-dicarboxylic acid [3-(4,4-diphenylpiperidine-1-yl)-propyl] ester methyl ester (710 mg, 1.16 mmol, 1.0 equiv) in EtOH (5 mL) was added a solution of HCl in ether (1.0 M, 1.5 mL, 1.5 mmol, 1.3 equiv). The solvents were removed and the residue was dissolved in CH$_2$Cl$_2$. This solution was added dropwise to 25 mL of ether to afford, after filtration, 500 mg of yellow crystalline solid: m.p. 152–153° C.. Anal. Calcd. for C$_{36}$H$_{39}$N$_3$O$_6$.HCl: C, 66.92; H, 6.24; N, 6.50. Found: C, 66.70; H, 5.99; N, 6.27

EXAMPLE 9

6-Ethyl-4-(4-nitrophenyl)-2-((2-aminoethyl)oxy)methyl-5-carboxamido-3-(N-(4,4-diphenylpiperidin-4-yl)propyl) carboxamido-1,4-dihydropyridine (Scheme 1).

a. 3-(4,4-Diphenylpiperidin-1-yl)propionitrile. To a suspension of 4,4-diphenylpiperidine hydrochloride (0.195 g, 0.712 mmol) in EtOH (1.5 mL) was added Et$_3$N (0.25 mL, 1.8 mmol, 2.6 eq) followed by acrylonitrile (0.13 mL, 2.01 mmol, 2.8 eq). The resulting solution was stirred at room temperature under argon for 15 min and then concentrated. Water was added, and the mixture was extracted with EtOAc (3×10 mL). The combined organic extracts were dried (MgSO$_4$) and concentrated to give 170 mg (87%) of tan solid, which was characterized spectroscopically and used in the next reaction without purification.

b. 3-(4,4-Diphenylpiperidin-1-yl)propylamine. To a stirred solution of 3-(4,4-diphenylpiperidin-1-yl) propionitrile (2.00 g, 6.89 mmol) in anhydrous rHF (20 mL) under argon was added a solution of BH$_3$ in THF (1.0 M, 24.1 mL, 24 mmol, 3.5 eq) at room temperature. The mixture was refluxed for 4.5 h and then cooled to room temperature. Aqueous HCl (6 N, 50 mL) was added and stirring was continued for 1 h. The mixture was basified to pH 9 by addition of 6 N aq. NaOH, extracted with CH$_2$Cl$_2$ (3×10 mL), dried (MgSO$_4$) and concentrated. The residue was purified by flash chromatography (SiO$_2$, EtOAc-MeOH-isopropylamine 9:1:0 to 4:1:0.2) to give 1.35 g (66%) of tan solid, which was characterized spectroscopically.

c) (±)-6-Ethyl-4-(4-nitrophenyl)-2-(methyloxy)methyl-5 (2-cyanocarboethoxy)-3-(carbophenylmethoxy)-1,4-dihydropyridine: A mixture of 3.28 g of ethyl 4-methoxy-3-oxo-butanoate (20.5 mmol) and 4.43 g of benzyl alcohol (41.0 mmol) were heated at 140–150 ° C.. (10–15) for 2 hrs. The reaction mixture was cooled, diluted with 20 mL of ethanol (denatured), 1.90 g of ammonium acetate (24.6 mmol) was added, and the resulting mixture was heated at reflux temperature for 1.5 hrs. The reaction mixture was cooled and 5.27 g of 2-cyanoethyl 2-(4-nitrobenzilidino)-3-oxopentanoate was added to the reaction mixture. The resulting mixture was heated at reflux temperature for 2 hrs, cooled, and solvent was removed in vacuo. The crude product was chromatographed on 550 g of silica packed with 10% EtOAc-hexane. The column was eluted with 20% (2 L), and 30% EtOAc-hexane (4 L) to give 3.08 g (30%) of 6-ethyl-4-(4-nitrophenyl)-2-(methyloxy)methyl-5-(2-cyanocarboethoxy)-3-(carbophenylmethoxy)-1,4-dihydropyridine as a yellow oil with solidified on standing. The product was used in the next step after pectral characterization.

d) (±)-2-Ethyl-4-(4-nitrophenyl)-6-(methyloxy)methyl-3-(2-cyanocarboethoxy)-1,4-dihydropyridine-3-carboxylic Acid: A suspension of 2.86 g of 6-ethyl-4-(4-nitrophenyl)-2-(methyloxy)methyl-5-(2-cyanocarboethoxy)-3-carbophenylmethoxy)-1,4-dihydropyridine (5.66 mmol), 572 mg of 10% Pd/C, 70 mL of methanol, and 2.09 mL of formic acid were stirred at room temperature for 0.5 h. The reaction mixture was diluted with 30 rnL of chloroform, filtered through a pad of Celite 545. The filtrate was concentrated in vacuo, and the residue was chromatographed on 250 g of silica packed with 30% EtOAc-hexane. The column was eluted with 50% to 80% EtOAc-hexane (10% change/1 L) to give 1.33 g of 2-ethyl-4-(4-nitrophenyl)-6-(methyloxy) methyl-3-(2-cyanocarboethoxy)-1,4-dihydropyridine-3-carboxylic acid (57%) as a yellow oily solid. Anal. Calc. for $C_{20}H_{21}N_3O_7$: C, 57.83; H, 5.10; N, 10.12. Found: C, 57.78; H, 5.08; N, 9.99.

e) (±)-2-Ethyl-4-(4-nitrophenyl)-6-(methyloxy)methyl-3-(2-cyanocarboethoxy)-5-(N-(4,4-diphenylpiperidin-4-yl) propyl)carboxamido-1,4-dihydropyridine, Hemihydrate: A solution of 433 mg of 2-ethyl-4-(4-nitrophenyl)-6-(methoxy)methyl-3-(2-cyanocarboethoxy)-1,4-dihydropyridine-3-carboxylic acid (1.04 mmol), 401 mg of 1-(dimethylaminopropyl)-3-ethylcarbodiimide hydrochloride (DMAPECD) (2.09 mmol), and 153 mg of 4-dimethylaminopyridine (DMAP) (1.25 mmol) in 5 mL of dry dichloromethane were stirred at room temperature for 1 h. The reaction mixture was charged with 328 mg of N-(3-aminopropyl)-4,4-diphenylpiperidine (1.25 mmol), and the resulting solution was heated at reflux temperature for 2 hrs. The reaction mixture was cooled, and applied to 200 g of silica packed with 5% MeOH-EtOAc. The column was eluted with 10% to 20% MeOH-EtOAc (1 L/5% change) to afford 552 mg of 2-ethyl-4-(4-nitrophenyl)-6-(methyloxy)methyl-3-(2-cyanocarboethoxy)-5-(N-(4,4-diphenylpiperidin-4-yl)propyl)carboxamido-1,4-dihydropyridine (77%) as a yellow foamy solid: mp 120–125° C..; Anal. Calc. for $C_{40}H_{45}N_5O_6 \cdot 0.5H_2O$: C, 68.55; H, 6.62; N, 9.99. Found: C, 68.37; H, 6.26; N, 9.98.

f) (±)-2-Ethyl-4-(4-nitrophenyl)-6-(methyloxy)methyl-3-(N-(4,4-diphenylpiperidin-4-yl)propyl)carboxamido- 1,4-dihydropyridine-3-carboxylic Acid: A solution of 40 mg of NaOH in 2 mL of water was added to 530 mg of 2-ethyl-4-(4-nitrophenyl)-6-(methyloxy)methyl-3-(2-cyanoethoxy)-5-(N-(4,4-diphenylpiperidin-4-yl) propyl)carboxamido-1,4-dihydropyridine (0.766 mmol) in 10 mL of dioxane. The resulting mixture was stirred at room temperature for 1 h. The solvent was removed in vacuo, the residue was partitioned between 20 mL of water (containing 200 mg of NaOH) and EtOAc (10 mL), separated, and the organic layer was extracted with 2×5 mL of water. The combined aqueous extracts were acidified (concentrated HCl, pH=3–4), and the precipitated oil was extracted with 3×10 mL of dichloromethane. The combined organic extracts were dried ($Na_2SO_4$), and the solvent was removed in vacuo to afford 472 mg (97%) of 2-ethyl-4-(4-nitrophenyl)-6-(methoxy)methyl-5-(N-(4,4-diphenylpiperidin-4-yl)propyl)carboxamido-1,4-dihydropyridine-3-carboxylic acid as a yellow solid: mp 120–125° C.. (decomp.); Anal. Calc. for $C_{37}H_{42}N_4O_6 \cdot 2H_2O$: C, 65.86, H, 6.87; N, 8.30. Found: C, 65.52; H, 7.05; N, 7.89.

g. (±)-5-Ethyl-4-(4-nitrophenyl)-2-(methyloxy)methyl-3-(N-(4,4-diphenylpiperidin-4-yl)propyl)carboxamido-5-carboxamido-1,4-dihydropyridine, Hemihydrate: A mixture of 70.0 mg of 2-ethyl-4-(4-nitrophenyl)-6-(methyloxy) methyl-5-(N-(4,4-diphenylpiperidin-4-yl)propyl) carboxamido-1,4-dihydropyridine-3-carboxylic acid (0.110 mmol), 90.5 mg of DCC (0.435 mmol), and 16.0 mg of DMAP (0.132 mmol) in 5 mL of dry dichloromethane were stirred at room temperature for 1 hr followed by addition of 5 mL of concentrated ammonia. The resulting mixture was heated at reflux temperature for 16 hrs, cooled, filtered, dichloromethane was removed in vacuo, and the residue was dissolved in 5 mL of ethyl acetate (a small amount of dichloromethane was added to make the mixture homogeneous). The ethyl acetate solution was sequentially washed with aqueous saturated ammonium chloride solution (3×2 mL), aqueous sodium carbonate solution (2 mL), dried ($Na_2SO_4$), and the solvent was removed in vacuo. The residue was chromatographed on 200 g of silica packed with $NH_3$ (2 M in MeOH)-MeOH-$CHCl_3$ (1:2:40). The column was eluted with the same solvent to give 21.0 mg of 5-ethyl-4-(4-nitrophenyl)-2-(methyloxy)methyl-3-(N-(4,4-diphenylpiperidin-4-yl)propyl)carboxamido-5-carboxamido-1,4-dihydropyridine as a yellow solid: mp 89° C.. (decomp.); Anal. Calc. for $C_{37}H_{43}N_5O_5 \cdot 0.5\ H_2O$: C, 68.72; H, 6.86; N, 10.83. Found: C, 68.40; H, 6.91; N, 10.41 h) Ethyl 4-(2,2,2-Trifluoroethyl)oxy-3-oxobutanoate: A solution of 5.00 g of trifluoroethanol (50.0 mol.) in 5 ml of dry THF was added dropwise, over a period of 0.5 hr, to a stirred mixture of 4.00 g of 60% dispersion of NaH (100 mol.), 1.61 g of tetraburylammonium bromide (5.0 mol.), and 830 mg of NaI (5.0 mol.) in 20 ml of dry THF (water bath). The resulting mixture was stirred for 0.5 hrs, cooled to −30 ° C.., and a solution of 8.23 g of ethyl 4-chloro-3-oxobutanoate (50.0 mol.) in 10 ml of dry THF was added dropwise, over a period of 15 min, to the reaction mixture. The reaction mixture was warmed to 0° C.. over a period of 2 hrs, and stirred at room temperature for 36 hrs. The reaction mixture was quenched with 5 ml of ethanol, partitioned between 100 ml of EtOAc and 100 ml of 10% aqueous HCl solution, separated, extracted with 2×40 ml of EtOAc, the combined organic extracts were dried ($Na_2SO_4$), and the solvent was removed in vacuo. The crude product was chromatographed on 400 g of silica packed with 5% EtOAc-hexane. The column was eluted with 5 to 25% EtOAc-hexane (1 L/5% change) to afford 8.75 g (77%) of Ethyl 4-(2,2,2-trifluoroethyl)oxy-3-oxobutanoate as a slightly yellow oil. The product was used in the next step after spectral characterization.

i) 2-Cyanoethyl 4-(2,2,2-Trifluoroethyl)oxy-3-oxobutanoate: A mixture of 4.04 g of ethyl 4-(2,2,2- trifluoroethyl)oxy-3-oxobutanoate (17.7 mol.) and 2.55 g of 3-hydroxypropionitrile (35.9 mol.) was heated at reflux temperature at a bath temperature of 135–150° C.. at 10 torr for 6 hrs. The reflux condenser was replaced with a distillation head and the product was distilled under reduced pressure to give 4.26 g (96%) of the desired product as a viscous oil: bp 155–158° C.. (1.5). The product was used in the next step after spectral characterization.

j) (±)-6-Methyl-4-(4-nitrophenyl)-2-((2,2,2-Trifluoroethyl)oxy)methyl-5-carboxamido-1,4-dihydrbpyridine-3-carboxylic Acid: A mixture of 1.07 g of 2-cyanoethyl 4-(2,2,2-trifluoroethyl)oxy-3-oxobutanoate (4.23 mol.) and 391 mg of ammonium acetate (5.08 mol.) in 5 ml of ethanol were heated at reflux temperature for 15 min, cooled, and 2-(p-nitrobenzilidino)acetoacetamide (4.23 mol.) was added to the reaction mixture. The resulting mixture was heated at reflux temperature for 4.5 hrs, cooled, and a solution of 406 mg of NaOH (10.2 mol.) in 5 ml of water was added to the reaction mixture. The resulting mixture was stirred at room temperature for 0.5 hr. The solvent was removed in vacuo, and the residue was partitioned between EtOAc (20 ml) and water (20 ml containing 300 mg of NaOH), separated, and the organic layer was extracted with 2×10 ml of water (each containing 150 mg of NaOH). The combined aqueous extracts were filtered, acidified to pH 2–3 with concentrated HCl, and the separated oil was extracted with 50 and then 2×20 ml of EtOAc. The combined EtOAc extracts were dried (MgSO$_4$), and the solvent was removed in vacuo. The crude product crystallized upon trituration with ethyl acetate to give 450 mg of 6-methyl-4-(4-nitrophenyl)-2-((2,2,2-trifluoroethyl)oxy)methyl-5-carboxamido-1,4-dihydropyridine-3-carboxylic acid (26%) as a yellow crystalline solid: mp 184° C.. (decomp.); Anal. Calc. for $C_{17}H_{16}N_3F_3O_6$: C, 49.16; H, 3.88; N, 10.12. Found: 48.81; H, 3.97; N, 9.80.

k) (±)-6-Methyl-4-(4-nitrophenyl)-2-((2,2,2-trifluoroethyl)oxy)methyl-5-carboxamido-3-N-((4,4-diphenylpiperidin-4-yl)propyl)carboxamido-1,4-dihydropyridine: A mixture of 102 mg of 6-methyl-4-(4-nitrophenyl)-2-((2,2,2-trifluoroethyl)oxy)methyl-5-carboxamido-1,4-dihydropyridine-3-carboxylic acid (0.230 mol.), 72.0 mg of N-3-aminopropyl-4,4-diphenylpiperidine (0.276 mol.), 119 mg of DCC (0.575 mol.), and 31.0 mg of DMAP (0.253 mol.) in 5 ml of dry dichloromethane were heated at reflux temperature for 3 hrs, cooled, filtered, and the solvent was removed in vacuo. The residue was dissolved in 5 ml of EtOAc, and sequentially washed with saturated aqueous ammonium chloride solution (2×2 ml), saturated aqueous sodium carbonate solution (2 ml), dried (Na$_2$SO$_4$), and directly applied to 200 g of silica packed with 2N NH$_3$ (in methanol)-MeOH-CHCl$_3$ (1:2:20). The column was eluted with the same solvent system to afford 140 mg of product as a yellow solid (87%): mp 89° C.. (decomp.); Anal. Calc. for $C_{37}H_{40}N_5F_3O_5$: C, 64.24; H, 5.83; N, 10.12. Found: C, 63.90; H, 5.87; N, 9.66 l) (±)-6-Ethyl-4-(4-nitrophenyl)-2-((2-azidoethyl)oxy)methyl-5-(2-cyanocarboethoxy)-3-(1,1-dimethyl)carboethoxy-1,4-dihydropyridine: A mixture of 1.00 g of t-butyl 4-(2-azidoethoxy)-3-oxopentanoate (4.10 mol.) and concentrated ammonia (0.800 g, 24.6 mol.) in 1.5 ml of t-BuOH was stirred at room temperature 17 hrs. The solvent was remove in vacuo to a give a yellow viscous oil which was used in the next step after spectral characterization. A mixture of the resulting enamide, and 0.850 g of 2-cyanoethyl 2-benzilidino-3-oxopentanoate in 15 ml of t-BuOH was heated at reflux temperature for 5 hrs. The reaction mixture was concentrated in vacuo, and the crude product was chromatographed on silica (EtOAc-hexane, 1:3) to give 836 mg of 6-ethyl-4-(4-nitrophenyl)-2-((2-azidoethyl)oxy)methyl-5-(2-cyanocarboethoxy)-3-(1,1-dimethyl)carboethoxy-1,4-dihydropyridine (56%) as a yellow viscous oil: Anal. Calc. for $C_{25}H_{30}N_6O_7$: C, 57.02; H, 5.25; N, 15.95. Found: C, 56.77; H, 5.67; N, 15.69.

m) (±)-6-Ethyl-4-(4-nitrophenyl)-2-((2-azidoethyl)oxy)methyl-3-(1,1-dimethyl)carboethoxy-1,4-dihydropyridine-5-carboxylic Acid: A solution of 91 mg of sodium hydroxide (2.3 mol.) in 7.5 ml of water was added to a solution of 800 mg of 6-ethyl-4-(4-nitrophenyl)-2-((2-azidoethyl)oxy)methyl-5-(2-cyanocarboethoxy)-3-(1,1-dimethyl)carboethoxy-1,4-dihydropyridine (1.52 mol.) in 7.5 ml of dioxane. The resulting mixture was stirred at room temperature for 3.5 hrs. The reaction mixture was washed with ether (10 ml), and the ether extract was backwashed with water (basic at pH=9–10). The combined aqueous extracts were acidified (pH=4), and the precipitated solid was collected to give the desired acid as a yellow solid (600 mg, 83%) : mp 170–173° C..; Anal. Calc. for $C_{22}H_{27}N_5O_7$: C, 55.80; H, 5.76; N, 14.78. Found: C, 56.07; H, 5.76; N, 14.73.

n) (±)-6-Ethyl-4-(4-nitrophenyl)-2-((2-azidoethyl)oxy)methyl-5-(N-(4,4-diphenylpiperidin-4-yl)propyl)carboxamido-3-(1,1-dimethyl)carboethoxy-1,4-dihydropyridine: A mixture of 300 mg of 6-ethyl-4-(4-nitrophenyl)-2-((2-azidoethyl)oxy)methyl-3-(1,1-dimethyl)carboethoxy-1, 4-dihydropyridine-5-carboxylic acid (0.634 mol.), 182 mg of DMAPECD, and 93 mg of DMAP in 8 ml of dry dichloromethane were stirred at room temperature for 3 hrs. The reaction mixture was charged with 216 mg of N-(3-aminopropyl)-4,4-diphenylpiperidine (0.824 mol.), and heated at reflux temperature for 19 hrs. The reaction mixture was concentrated in vacuo and the crude product was chromatographed (5% MeOH-EtOAc) to give 400 mg of desired product (86%) as a yellow foamy solid: mp 62–67° C..; Anal. Calc. for $C_{42}H_{51}N_7O_6$: C, 67.26; H, 6.89; N, 13.07. Found: C, 66.96; H, 6.79; N, 12.87.

o) (±)-6-Ethyl-4-(4-nitrophenyl)-2-((2-aminoethyl)oxy)methyl-5-(N-(4,4-diphenylpiperidin-4-yl)propyl)carboxamido-3-(1,1-dimethyl)carboethoxy-1,4-dihydropyridine: A solution of 136 mg of 6-ethyl-4-(4-nitrophenyl)-2-((2-azidoethyl)oxy)methyl-5-(N-(4,4-diphenylpiperidin-4-yl)propyl)carboxamido-3-(1,1-dimethyl)carboethoxy-1,4-dihydropyridine (0.180 mol.), 57 mg of triphenylphosphine (0.22 mol.), and 5 ml of water in 3.5 ml of ethyl acetate were stirred at room temperature for 13 hrs. The reaction mixture was concentrated in vacuo and the crude product was chromatographed on silica (2N NH$_3$ (in methanol)-MeOH-CHCl$_3$, 1:1:9) to give 25 mg of ethyl-4-(4-nitrophenyl)-2-((2-aminoethyl)oxy)methyl-5-(N-(4,4-diphenylpiperidin-4-yl)propyl)carboxamido-3-(1,1-dimethyl)carboethoxy-1,4-dihydropyridine as a light yellow foamy solid: mp 84–89° C..; Anal. Calc. for $C_{42}H_{53}N_5O_6 \cdot 0.7H_2O$: C, 68.49; H, 7.44; N, 9.51. Found: C, 68.14; H, 7.00; N, 9.41.

p) (±)-2-Ethyl-4-(4-nitrophenyl)-6-((2-azidoethyl)oxy)methyl-3-(2-cyanocarboethoxy)-1,4-dihydropyridine-5-carboxylic Acid: A mixture of 2.90 g of 6-ethyl-4-(4-nitrophenyl)-2-( (2-azidoethyl)oxy)methyl-5-(2-cyanocarboethoxy)-3-(1, 1-dimethyl) carboethoxy-1,4-dihydropyridine (5.51 mol.) in 10 ml of formic acid was stirred for 1.5 hrs, solvent removed in vacuo. The crude product was triturated with EtOAc and a small amount of hexane and the resulting precipitated yellow product was collected (700 mg): mp 150° C.. (decomp.). The product was used in the following steps after spectral characterization.

q) (±)-2-Ethyl-4-(4-nitrophenyl)-6-((2-azidoethyl)oxy)methyl-5-(N-(4,4-diphenylpiperidin-4-yl)propyl)

carboxamido-3-(2-cyanocarboethoxy)-1,4-dihydropyridine: A solution of 700 mg of ethyl-4-(4-nitrophenyl)-6-((2-azidoethyl)oxy)methyl-3-(2-cyanocarboethoxy)-1,4-dihydropyridine-5-carboxylic acid (1.49 mol.), 461 mg of DCC (2.23 mol.), and 145 mg of DMAP (1.19 mol.) in 10 ml of dry dichloromethane were stirred at room temperature for 1.5 hrs. The reaction mixture was charged with 570 mg of N-(3-aminopropyl)-4,4-diphenylpiperidine (1.93 mol.), and the reaction mixture was stirred for 13 hrs. The reaction mixture was filtered and applied to a flash chromatography column (silica, MeOH-EtOAc 5% to 10%) to give 815 mg of the desired product (73%) as a yellow foamy solid: mp 63–67° C..; Anal. Calc. for $C_{41}H_{46}N_8O_6 \cdot H_2O$: C, 64.38; H, 6.33; N, 14.65. Found: C, 64.72; H, 6.12; N, 14.62.

r) (±)-2-Ethyl-4-(4-nitrophenyl)-6-((2-azidoethyl)oxy)methyl-5-(N-(4,4-diphenylpiperidin-4-yl)propyl)carboxamido-1,4-dihydropyridine-3-carboxylic Acid: A solution of sodium hydroxide (30 mg) in 2 ml of water was added to a solution of 356 mg of 2-ethyl-4-(4-nitrophenyl)-6-((2-azidoethyl)oxy)methyl-5-(N-(4,4-diphenylpiperidin-4-yl)propyl)carboxamido-3-(2-cyanocarboethoxy)-1,4-dihydropyridine (0.500 mol.) in 2 ml of dioxane. The resulting mixture was stirred at room temperature for 2 hrs. The solvent was removed in vacuo. The residue was dissolved in 10 ml of water and extracted with a 1:1 mixture of ether-hexane (10 ml). The aqueous extract was acidified to pH 4 (concentrated HCl), and the precipitated yellow solid was collected to give 283 mg of 2-ethyl-4-(4-nitrophenyl)-6-((2-azidoethyl)oxy)methyl-5-(N-(4,4-diphenylpiperidin-4-yl)propyl)carboxamido-1,4-dihydropyridine-3-carboxylic acid (82%): mp 118° C.. (decomp.); Anal. Calc for $C_{38}H_{43}N_7O_6$: C, 65.78; H, 6.26; N, 14.12. Found: C, 65.55; H, 6.31; N, 13.96.

s) (±)-6-Ethyl-4-(4-nitrophenyl)-2-((2-azidoethyl)oxy)methyl-5-carboxamido-3-(N-(4,4-diphenylpiperidin-4-yl)propyl)carboxamido-1,4-dihydropyridine: A solution of 600 mg of 2-ethyl-4-(4-nitrophenyl)-6-((2-azidoethyl)oxy)methyl-5-(N-(4,4-diphenylpiperidin-4-yl)propyl)carboxamido- 1,4-dihydropyridine-3-carboxylic acid (0.865 mol.), DCC (357 mg, 1.73 mol.), and DMAP (85 mg, 0.692 mol.) in 15 ml of dry dichloromethane was stirred at room temperature for 2 hrs. The reaction mixture was charged with 522 mg of concentrated ammonia solution, and the reaction mixture was stirred at room temperature for 3 days. The reaction mixture was filtered, concentrated in vacuo and the crude product was chromatographed (silica, MeOH-EtOAc, 1:9, 1:8, 1:4) to give 528 mg of product as a yellow foamy solid (88%): mp 88–93° C..; Anal. Calc. for $C_{38}H_{44}N_8O_5 \cdot 0.5H_2O$: C, 65.03; H, 6.46; N, 15.97. Found: C, 64.80; H, 5.96; N, 15.88.

t) (±)-6-Ethyl-4-(4-nitrophenyl)-2-((2-aminoethyl)oxy)methyl-5-carboxamido-3-(N-(4,4-diphenylpiperidin-4-yl)propyl)carboxamido-1,4-dihydropyridine: A solution of 61 mg of 6-ethyl-4-(4-nitrophenyl)-2-((2-azidoethyl)oxy)methyl-5-carboxamido-3-(N-(4,4-diphenylpiperidin-4-yl)propyl)carboxamido-1,4-dihydropyridine (0.088 mol.), triphenylphosphine (30 mg, 0.114 mol.), and water (2.5 mg, 0.141 mol.) in 1 ml EtOAc was stirred at room temperature for 3 days. The reaction mixture was concentrated in vacuo, and chromatographed (silica, $NH_3$ (2N in methanol) :MeOH:$CHC_3$ (1:2:20)) to give 32 mg of 6-ethyl-4-(4-nitrophenyl)-2-((2-aminoethyl)oxy)methyl-5-carboxamido-3-(N-(4,4-diphenylpiperidin-4-yl)propyl)carboxamido-1,4-dihydropyridine (55%) as a yellow solid: mp 98–103° C..; Anal. Calc. for $C_{38}H_{46}N_6O_5 \cdot 1.0H_2O \cdot 0.2CH_2Cl_2$: C, 65.38; H, 6.95; N, 11.97. Found: C, 65.39; H, 6.58; N, 11.44.

Using trimethylphosphine as the reducing agent, on a large scale (3 mol.), a 93% yield of the 6-ethyl-4-(4-nitrophenyl)-2-((2-aminoethyl)oxy) methyl-5-carboxamido-3-(N-(4,4-diphenylpiperidin-4-yl)propyl)carboxamido-1,4-dihydropyridine was realized. The product from this batch had the following microanalytical data: Anal. Calc. for $C_{38}H_{46}N_6O_5 \cdot 1.3 H_2O$: C, 66.12; H, 7.10; N, 12.18. Found: C, 66.17; H, 6.69; N, 12.09 u) The enantiomers of 6-ethyl-4-(4-nitrophenyl)-2-((2-aminoethyl)oxy)methyl-5-carboxamido-3-(N-(4,4-diphenylpiperidin-4-yl)propyl)carboxamido-1,4-dihydropyridine were separated on a Chiracel AD (2 cm) column. The retention times on the semi-prep column were dependent on the column load. At a 60 mg load, the retention times were 128 and 228 minutes (hexane-ethanol-isopropanol (containing 3% diethylamine) 84:3:13). The retention times on the analytical Chiracel AD column (4.6 mm), using the same solvent mixture were 34 and 54 minutes (broad peaks). The plus isomer eluted first followed by the minus isomer. The purity of the final selected enantiomeric fractions were >99.9%.

(−)-6-Ethyl-4-(4-nitrophenyl)-2-((2-aminoethyl)oxy)methyl-5-carboxamido-3-(N-(4,4-diphenylpiperidin-4-yl)propyl)carboxamido-1,4-dihydropyridine: $[a]_{100}=-39.8$ (+)-6-Ethyl-4-(4-nitrophenyl)-2-((2-aminoethyl)oxy)methyl-5-carboxamido-3-(N-(4,4-diphenylpiperidin-4-yl)propyl)carboxamido-1,4 dihydropyridine: $[a]_{100}=+40.1$ Scheme 1
Synthetic Scheme for the preparation of 6-Ethyl-4-(4-nitrophenyl)-2-((2-aminoethyl)oxy)methyl-5-carboxamido-3-(N-(4,4-diphenylpiperidin-4-yl)-propyl)carboxamido-1,4-dihydropyridine, Example 9

Part I

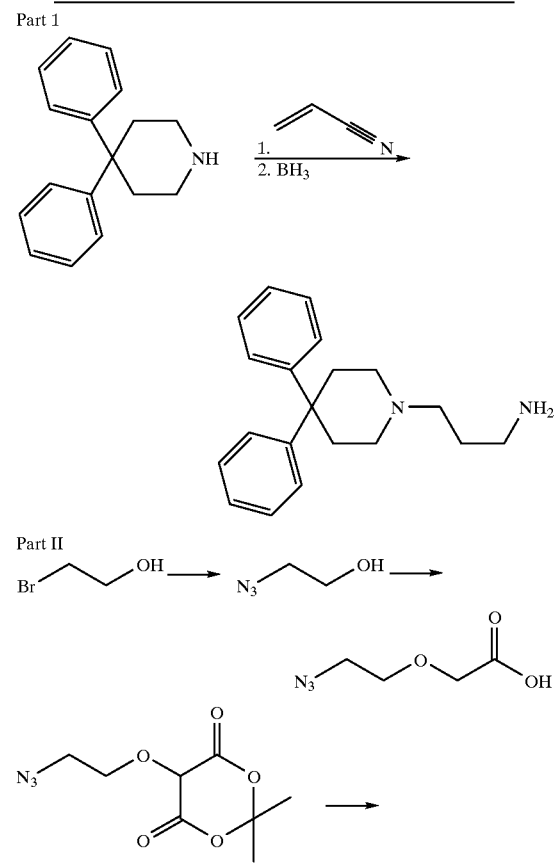

Part II

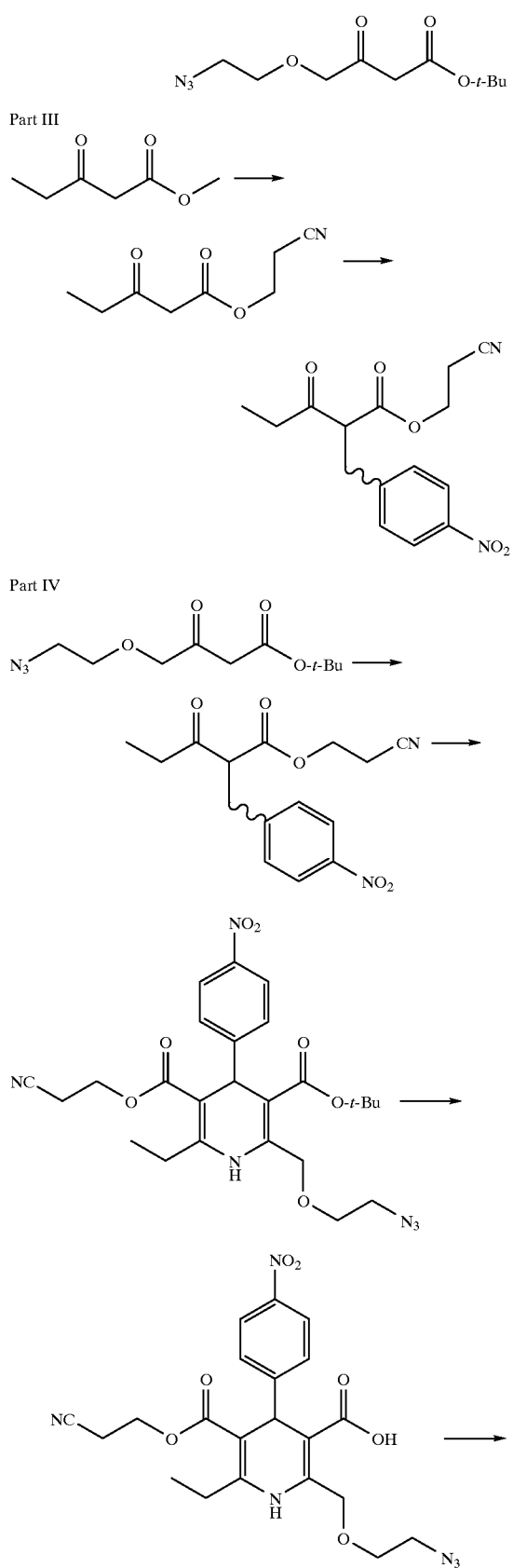
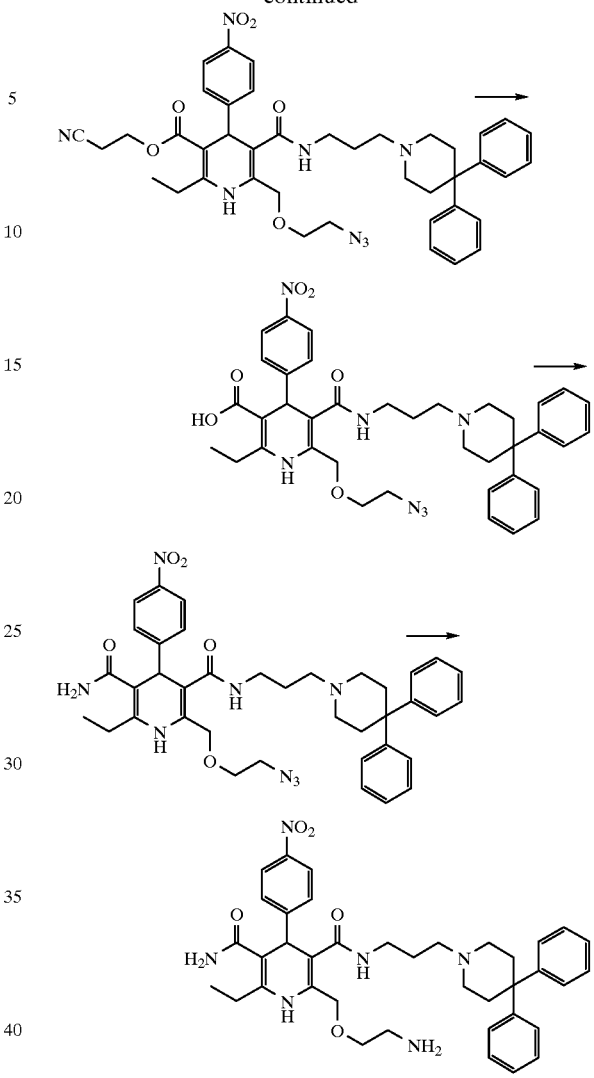

EXAMPLE 10

Protocol for the Determination of the Potency of $\alpha_1$ Antagonists

The activity of compounds at the different human receptors was determined in vitro using cultured cell lines that selectively express the receptor of interest. These cell lines were prepared by transfecting the cloned cDNA or cloned genomic DNA or constructs containing both genomic DNA and cDNA encoding the human α-adrenergic, serotonin, histamine, and dopamine receptors as follows:

$\alpha_{1A}$ Human Adrenergic Receptor: The entire coding region of α1A (1719 bp) (Sequence I.D. No. 1), including 150 basepairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequence were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1A/EXJ (expression vector containing the α1A receptor gene) and the plasmid pGCcos3neo (plasmid containing the aminoglycoside transferase gene) into LM(tk⁻), CHO, and NIH3T3 cells, using calcium phosphate technique. The cells were grown, in a controlled environment (37° C.., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 μg/ml streptomycin sulfate. Stable clones were then selected for resistance to the antibiotic G-418 (1 mg/ml), and membranes were harvested and assayed for their ability to bind [$^3$H]prazosin as described below (see "Radioligand Binding assays").

$α_{1B}$ Human Adrenergic Receptor: The entire coding region 5 of α1B (1563 bp) (Sequence I.D. No. 3), including 200 basepairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem cDNA fragment from λ ZapII into the expression vector. Stable cell line s were selected as described above.

Human $α_{1C}$ Adrenergic Receptor: The entire coding region of α1C (1401 bp) (Sequence I.D. No. 5), including 400 basepairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partiaL overlapping fragments: a 5' 0.6kb HincII genomic clone, a central 1.8 EcoRI hippocampal cDNA clone, and a 3' 0.6 Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above.

Radioligand Binding Assays: Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C.., and the supernatant was centrifuged at 30,000×g for 20 min at 4° C.. The pellet was suspended in 50 mM Tris-HCl. 1 mM $MgCl_2$, and 0.1% ascorbic acid at pH 7.5. Binding of the α1 antagonist [$^3$H]prazosin (0.5 nM, specific activity 76.2 Ci/mmol) to membrane preparations of LM(tk⁻) cells was done in a final volume of 0.25 ml and incubated at 37° C.. for 20 min. Nonspecific binding was determined in the presence of 10 μM phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

$α_2$ Human Adrenergic Receptors: To determine the potency of $α_1$ antagonists at the $α_2$ receptors, LM(tk⁻) cell lines stably transfected with the genes encoding the $α_{2A}$, $α_{2B}$, and $α_{2C}$ receptors were used. The cell line expressing the $α_{2A}$ receptor is designated L-$α_{2A}$, and was deposited on Nov. 6, 1992 under ATCC Accession No. CRL 11180. The cell line expressing the $α_{2B}$ receptor is designated L-NGC-$α_{2B}$, and was deposited on Oct. 25, 1989 under ATCC Accession No. CRL10275. The cell line expressing the $α_{2C}$ receptor is designated L-$α_{2C}$, and was deposited on Nov. 6, 1992 under ATCC Accession No. CRL-11181. Cell lysates were prepared as described above (see Radioligand Binding Assays), and suspended in 25 mM glycylglycine buffer (pH 7.6 at room temperature). Equilibrium competition binding assay were performed using [3H]rauwolscine (0.5 nM), and nonspecific binding was determined by incubation with 10μM phentolamine. The bound radioligand was separated by filtration through GF/B filters using a cell harvester.

Human Histamine $H_1$ Receptor: The coding sequence of the human histamine $H_1$ receptor, homologous to the bovine $H_1$ receptor, was obtained from a human hippocampal cDNA library, and was cloned into the eukaryotic expression vector pCEXV-3. The plasmid DNA for the $H_1$ receptor is designated pcEXV-H1, and was deposited on Nov. 6, 1992 under ATCC Accession No. 75346. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 min at 40° C.., and the supernatant was centrifuged at 30,000×g for 20 min. at 4° C.. The pellet was suspended in 37.8 mM $NaHPO_4$, 12.2 mM $KH_2PO_4$, pH 7.5. The binding of the histamine $H_1$ antagonist [$^3$H]mepyramine (1 nM, specific activity: 24.8 Ci/mM) was done in a final volume of 0.25 ml and incubated at room temperature for 60 min. Nonspecific binding was determined in the presence of 10 μM mepyramine. The bound radioligand was separated by filtration through GF/B filters using a cell harvester.

Human Histamine $H_2$ Receptor: The coding sequence of the human $H_2$ receptor was obtained from a human placenta genomic library, and cloned into the cloning site of PCEXV-3 eukaryotic expression vector. The plasmid DNA for the $H_2$ receptor is designated pcEXV-H2, and was deposited on Nov. 6, 1992 under ATCC Accession No. 75346. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 min at 40° C.., and the supernatant was centrifuged at 30,000×g for 20 min at 4° C.. The pellet was suspended in 37.8 mM $NaHPO_4$, 12.2 mM $K2PO_4$, pH 7.5. The binding of the histamine $H_2$ antagonist [$^3$H]tiotidine (5 nM, specific activity: 70 Ci/mM) was done in a final volume of 0.25 ml and incubated at room temperature for 60 min. Nonspecific binding was determined in the presence of 10 μM histamine. The bound radioligand was separated by filtration through GF/B filters using a cell harvester.

Human Serotonin Receptors:

$5HT_{1Dα}$, $5HT_{1Dβ}$, $5HT_{1E}$, $5HT_{1F}$ Receptors

The cell lysates of LM(tk-) clonal cell line stably transfected with the genes encoding each of these 5HT receptor-subtypes were prepared as described above. The cell line for the $5HT_{1Dα}$, receptor, designated as Ltk-8-30-84, was deposited on Apr. 17, 1990, and accorded ATCC Accession No. CRL 10421. The cell for the $5HT_{1Dβ}$receptor, designated as Ltk-11, was deposited on Apr. 17, 1990, and accorded ATCC Accession No. CRL 10422. The cell line for the $5HT_{1E}$ receptor, designated 5 $HT_{1E}$-7, was deposited on Nov. 6, 1991, and accorded ATCC Accession No. CRL 10913. The cell line for the $5HT_{1F}$ receptor, designated L-5-$HT_{1F}$, was deposited on Dec. 27, 1991, and accorded ATCC Accession No. ATCC 10957. These preparations were suspended in 50 mM Tris-HCl buffer (pH 7.4 at 37° C..) containing 10 mM $MgCl_2$, 0.2 mM EDTA, 10 μM pargyline, and 0.1% ascorbate. The potency of $\alpha_1$ antagonists was determined in competition binding assay by incubation for 30 minutes at 37° C.. in the presence of 5 nM [3H]serotonin. Nonspecific binding was determined in the presence of 10 $\mu$M serotonin. The bound radioligand was separated by filtration through GF/B filters using a cell harvester.

Human 5HT$_2$ Receptor: The coding sequence of the human 5T$_2$ receptor was obtained from a human brain cortex cDNA library, and cloned into the cloning site of pCEXV-3 eukaryotic expression vector. This construct was transfected into LM(tk-) cells by the DEAE-dextran method. Cells were harvested after 72 hours and lysed by sonication in 5 mM Tris-HCl, 5 mM EDTA, pH 7.5. This cell line was deposited with the ATCC on Oct. 31, 1989, designated as L-NGC-5HT$_2$, and was accorded ATCC Accession No. CRL 10287. The cell lysates were centrifuged at 1000 rpm for 5 minutes at 4° C.., and the supernatant was centrifuged at 30,000×g for 20 minutes at 4° C.. The pellet was suspended in 50 mM Tris-HCl buffer (pH 7.7 at room temperature) containing 10 mM MgSO$_4$, 0.5 mM EDTA, and 0.1% ascorbate. The potency of alpha-1 antagonists at 5HT$_2$ receptors was determined in equilibrium competition binding assays using [3H]ketanserin (1 nM). Nonspecific binding was defined by the addition of 10 $\mu$M mianserin. The bound radioligand was separated by filtration through GF/B filters using a cell harvester.

Human Dopamine D$_2$ Receptors: The potency of $\alpha_1$ antagonists at the D2 receptor was determined using membrane preparations from COS-7 cells transfected with the gene encoding the human D$_2$ receptor. The coding region for the human D2 receptor was obtained from a human striatum cDNA library, and cloned into the cloning site of PCDNA 1 eukariotic expression vector. The plasmid DNA for the D$_2$ receptor is designated pcEXV-D2, and was deposited on Nov. 6, 1992 under ATCC Accession No. ATC 75344. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 minutes at 4° C.., and the supernatant was centrifuged at 30,000×g for 20 minutes at 4° C.. The pellet was suspended in 50 mM Tris-HCl (pH 7.4) containing 1 mM EDTA, 5 mM KCl, 1.5 mM CaCl$_2$, 4 mM MgCl$_2$, and 0.1% ascorbic acid. The cell lysates were incubated with [3H]spiperone (2 nM), using 10 $\mu$M (+)Butaclamol to determine nonspecific binding.

Other Dopamine receptors are prepared by known methods (D$_3$: Sokoloff, P. et al., Nature, 347, 146 (1990), and deposited with the European Molecular Biological Laboratory (EMBL) Genbank as X53944; D$_4$: Van Tol, H. H. M., et al., Nature, 350, 610 (1991), and deposited with EMBL Genbank as X58497; D$_5$: Sunahara, R. K., et al., Nature, 350, 614 (1991), and deposited with EMBL Genbank as X58454-HU HD 5DR).

Determination of the Activity of $\alpha_1$ Antagonists at Calcium Channels

The potency of $\alpha_1$ antagonists at calcium channels was determined in competition binding assays of [3H] nitrendipine to membrane fragments of rat cardiac muscle, essentially as described by Glossman and Ferry (Methods in Enzymology 109:513–550, 1985). Briefly, the tissue was minced and homogenized in 50 mM Tris-HCl (pH 7.4) containing 0.1 mM phenylmethylsulfonyl fluoride. The homogenates were centrifuged at 1000 g for 15 minutes, the resulting supernatant was centrifuged at 45,000 g for 15 minutes. The 45,000 g pellet was suspended in buffer and centrifuged a second time. Aliquots of membrane protein were incubated for 30 minutes at 37° C.. in the presence of [3H]nitrendipine (1 nM), and nonspecific binding was determined in the presence of 10 $\mu$M nifedipine. The bound radioligand was separated by filtration through GF/B filters using a cell harvester.

EXAMPLE 11

Functional Properties of $\alpha_1$ Antagonists in the Human Prostate

The efficacy of $\alpha_1$ adrenergic antagonists for the treatment of benign prostatic hyperplasia (BPH) is related to their ability to elicit relaxation of prostate smooth muscle. An index of this efficacy can be obtained by determining the potency of $\alpha_1$ antagonists to antagonize the contraction of human prostatic tissue induced by an $\alpha_1$ agonist "in vitro". Furthermore, by comparing the potency of subtype selective $\alpha_1$ antagonists in binding assays using human $\alpha_1$ receptors with their potency to inhibit agonist-induced smooth muscle contraction, it is possible to determine which of the $\alpha_1$ adrenergic receptor subtypes is involved in the contraction of prostate smooth muscle.

Methods: Prostatic adenomas were obtained at the time of surgery from patients with symptomatic BPH. These were cut into longitudinal strips of 15 mm long and 2–4 mm wide, and suspended in 5 ml organ baths containing Krebs -buffer (pH 7.4). The baths were maintained at 37° C.. and continuously oxygenated with 5% CO$_2$ and 95% O$_2$. Isometric tension was measured with a Grass Instrument FT03 force transducer interfaced with a computer. Tissue strips were contracted with varying concentrations of phenylephrine after incubating for 20 minutes in the absence and presence of at least three different concentrations of antagonist. Dose-response curves for phenylephrine were constructed, and the antagonist potency (pA$_2$) was estimated by the dose-ratio method. The concentration of some antagonists in the tissue bath was assessed by measuring the displacement of [3H] prazosin by aliquots of the bath medium, using membrane preparations of the cloned human $\alpha_{1C}$ receptor. This control was necessary to account for losses of antagonist due to adsorption to the tissue bath and/or metabolism during the time the antagonists were equilibrated with the prostate tissue.

Figure 2A:
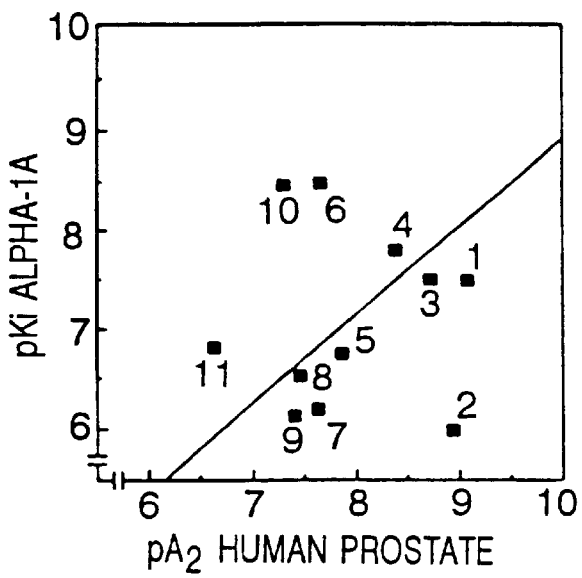
FIG. 2
Figure 2B:
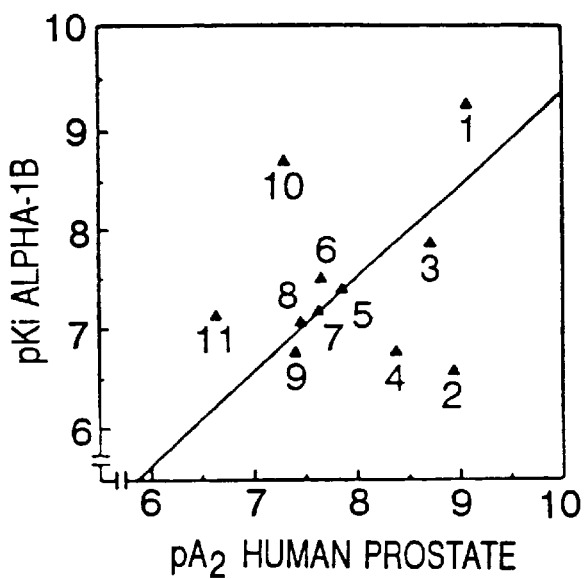
Figure 2C:
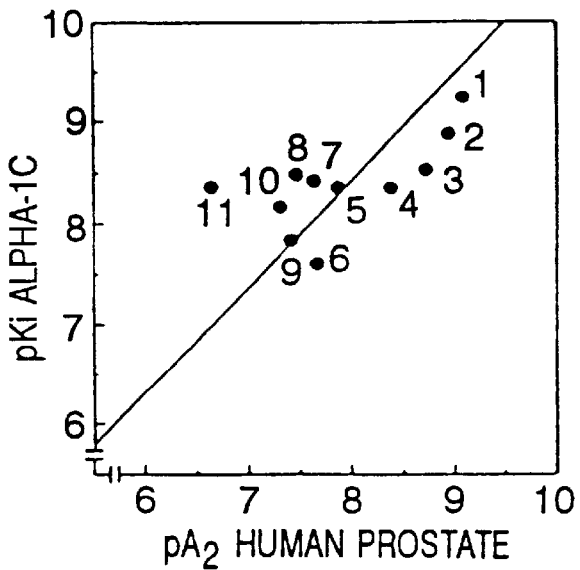

Results:

Table 1 shows that the pA$_2$ values measured for a series of $\alpha_1$ antagonists in human prostate tissue correlate closely (r=0.76) with the corresponding pK$_i$ values measured in the $\alpha_{1C}$ receptor assays. In contrast, the human prostate pA$_2$ values correlate poorly with the pK$_i$ values measured at the $\alpha_{1A}$ (r=−0.06) and $\alpha_{1B}$ (r=−0.24) adrenergic receptors. (See FIG. 2 (Panels A–C). Thus, antagonists which are more potent at blocking the $\alpha_{1C}$ adrenergic receptor are more effective at blocking the contraction of the human prostate than antagonists which are more potent at the $\alpha_{1A}$ or $\alpha_{1B}$ adrenergic receptors. In addition, antagonists which are selective for the $\alpha_{1C}$ receptor will have a better therapeutic ratio than nonselective $\alpha$ antagonists.

With SNAP 5036 (11), the low pA$_2$ observed in the prostate may be attributed to tissue absorption or metabolism.

Table 2 illustrates the cross reactivity of $\alpha_1$ antagonists at other receptors such as $\alpha_{2A}$, $\alpha_{2B}$, $\alpha_{2C}$, histamine H$_1$, H$_2$, serotonin 5-HT$_{1D\alpha}$, 5-HT$_{1D\beta}$, 5-HT$_{1E}$, 5-HT$_{1F}$, 5-HT$_2$, and dopamine D$_2$. Only compounds SNAP 5036, 5041, and 5089 have binding affinities which are greater than ten-fold higher at $\alpha_{1C}$ receptors than the binding affinities at other receptors.

Tables 3, 4 and 5 show cross reactivity of alpha-1 agonists at cloned human receptors. Table 6 shows a comparison of alpha-1 agonist cross reactivity between human neuronal receptors and human alpha-1C receptor.

TABLE 1

COMPARISON OF THE BINDING POTENCY ($pK_1$) OF ALPHA-1 ANTAGONISTS IN CLONED HUMAN RECEPTORS AND THEIR PROTENCY ($pA_2$) TO INHIBIT PROSTATE SMOOTH MUSCLE CONTRACTION

|   | Compound | Human Alpha-1 Adrenergic ($pK_1$) α1A | α1B | α1C | Human Prostate (pA) |
|---|----------|------|------|------|------|
| 1 | Prazosin | 9.48 | 9.26 | 9.23 | 9.08 |
| 2 | Compound 2 | 5.98 | 6.51 | 8.87 | 8.94 |
| 3 | A-30380 | 7.49 | 7.86 | 8.52 | 8.72 |
| 4 | 5-Methyl-Urapidil | 7.79 | 6.77 | 8.35 | 8.38 |
| 5 | Indoramin | 6.74 | 1.39 | 8.35 | 7.88 |
| 6 | SKF-104858 | 8.48 | 1.50 | 7.60 | 7.68 |
| 7 | Compound 7 | 6.82 | 7.18 | 8.42 | 7.63 |
| 8 | Compound 8 | 8.52 | 1.07 | 8.48 | 7.46 |
| 9 | Compound 9 | 6.12 | 6.76 | 7.83 | 7.41 |
| 10 | Terazosin | 8.46 | 8.71 | 8.16 | 7.30 |
| 11 | Compound 11 | 6.81 | 7.14 | 8.36 | 6.64 |

TABLE 2

CROSS REACTIVITY OF $\alpha_1$ ANTAGONISTS AT CLONED HUMAN RECEPTORS ($pK_1$)

| Compound | $\alpha_1$ Adrenergic α1A | α1B | α1C | $\alpha_2$ Adrenergic α2a | a2b | α2c | Histamine H1 | H2 | Serotonin 5HT1Dα | 5HT1Dβ | 5HT1E | 5HT1F | 5HT2 | Dopamine D2 | Calcium Channel |
|---|---|---|---|---|---|---|---|---|---|---|---|---|---|---|---|
| Terazosin | 8.46 | 8.71 | 8.16 | 6.26 | 7.51 | 6.64 | 4.00 | 5.04 | <6.0 | <6.0 | <5.0 | <5.0 | <5.0 | <5.0 | 5.19 |
| Prazosin | 9.48 | 9.26 | 9.23 | 6.76 | 7.64 | 7.65 | 4.00 | 5.19 | <5.0 | <5.0 | ND | ND | <6.0 | <5.0 | 4.57 |
| 5-Methylurapidil | 7.79 | 6.77 | 8.35 | 6.63 | 1.38 | 6.88 | 5.16 | 4.47 | 7.30 | 6.82 | ND | ND | <6.0 | <5.0 | ND |
| Indoramin | 6.74 | 7.39 | 8.35 | 4.94 | 5.72 | 5.22 | 7.37 | 5.63 | <6.0 | <6.0 | <5.0 | <5.0 | <7.0 | <8.0 | 4.53 |
| Compound 11 | 6.81 | 7.14 | 8.36 | 6.86 | 6.90 | 6.92 | 5.74 | 7.45 | <6.0 | <6.0 | <5.0 | <5.0 | <7.0 | <6.0 | 5.18 |
| A-30360 | 7.49 | 7.88 | 8.52 | 6.69 | 6.37 | 6.23 | 6.03 | 5.77 | <6.0 | <6.0 | <5.0 | <5.0 | <8.0 | <9.0 | 5.26 |
| Compound 7 | 6.82 | 7.18 | 8.42 | 6.19 | 6.07 | 6.09 | 7.59 | 6.02 | <6.0 | <5.0 | <5.0 | <5.0 | <8.0 | <7.0 | 4.79 |
| Compound 9 | 6.12 | 6.76 | 7.83 | 5.80 | 5.69 | 5.90 | 7.29 | 5.44 | <6.0 | <6.0 | <5.0 | <5.0 | <7.0 | <7.0 | 4.44 |
| SKF-104858 | 8.48 | 7.50 | 7.60 | 7.30 | 8.49 | 7.60 | 5.59 | 5.84 | <7.0 | <7.0 | <6.0 | <7.0 | <8.0 | <7.0 | 4.68 |
| S-Niguidipine | 6.72 | 7.07 | 8.75 | 6.19 | 5.24 | 6.43 | 6.78 | 6.24 | ND | ND | ND | ND | <7.0 | <7.0 | 8.04 |
| Compound 8 | 6.52 | 7.07 | 8.48 | 5.99 | 6.12 | 5.77 | 6.67 | 6.11 | <6.0 | <5.0 | <5.0 | <5.0 | <7.0 | <6.0 | 6.87 |
| Compound 2 | 5.98 | 6.57 | 8.87 | 5.48 | 5.93 | 5.88 | 7.16 | 7.48 | <7.0 | <6.0 | <5.0 | <5.0 | <6.0 | <7.0 | 6.13 |

ND = Not Determined

TABLE 3

CROSS REACTIVITY OF $\alpha_1$ ANTAGONISTS AT CLONED HUMAN RECEPTORS

| pK1 Compound | Alpha-1 Adrenergic α1A MEAN | SEM | α18 MEAN | SEM | α1C MEAN | SEM | Alpha-2 Adrenergic α2a MEAN | SEM | a2b MEAN | α2c | Histamine H1 | H2 | Calcium Channel |
|---|---|---|---|---|---|---|---|---|---|---|---|---|---|
| Terazosin | 8.48 | | 8.71 | | 8.16 | | 6.26 | | 7.51 | 6.64 | 4.00 | 5.04 | 5.19 |
| Prazosin | 9.48 | | 9.28 | | 9.23 | | 6.76 | | 7.64 | 7.65 | 4.00 | 5.19 | 4.57 |
| 5-Methylurapidil | 7.79 | | 8.77 | | 8.35 | | 8.83 | | 7.38 | 6.88 | 5.18 | 4.47 | ND |
| Indoramin | 8.74 | | 7.39 | | 8.35 | | 4.94 | | 5.72 | 5.22 | 7.38 | 5.83 | 4.53 |
| Compound 11 | 8.81 | | 7.14 | | 8.38 | | 6.88 | | 8.90 | 6.92 | 5.74 | 7.45 | 5.18 |
| A-30360 | 7.49 | | 7.88 | | 8.52 | | 6.69 | | 8.31 | 8.23 | 6.03 | 5.77 | 5.28 |
| Compound 7 | 8.82 | | 7.18 | | 8.42 | | 8.19 | | 8.07 | 8.09 | 7.59 | 8.02 | 4.79 |
| Compound 9 | 8.12 | | 8.78 | | 7.83 | | 5.80 | | 5.69 | 5.90 | 7.29 | 5.44 | 4.44 |
| SKF-104858 | 8.48 | | 7.50 | | 7.80 | | 7.30 | | 8.49 | 7.80 | 5.59 | 5.84 | 4.88 |
| S-Niguidipine | 8.12 | | 7.07 | | 8.75 | | 8.19 | | 5.24 | 8.43 | 8.78 | 6.24 | 8.04 |
| Compound 8 | 6.52 | | 7.01 | | 8.48 | | 5.99 | | 6.12 | 5.77 | 8.87 | 6.11 | 6.87 |
| Compound 2 | 5.98 | | 8.57 | | 8.87 | | 5.48 | | 5.93 | 5.88 | 7.18 | 7.48 | 6.13 |

TABLE 3-continued

Comparison of Alpha-1 Antagonist Crossreactivity Between Human Neuronal Receptors and Human Alpha-1c

| pK1 Compound | 5HT1Da | 5HT1Db | 5HT1E | 5HT1F | 5HT2 | D2 | Ca Chann |
|---|---|---|---|---|---|---|---|
| Terazosin | 6.00 | 6.00 | 5.00 | 5.00 | 5.00 | 5.00 | 5.19 |
| Prazosin | 5.00 | 5.00 | ND | ND | 6.00 | 5.00 | 4.57 |
| 5-Methylurapidil | 7.30 | 6.82 | ND | ND | 6.00 | 5.00 | ND |
| Indoramin | 6.00 | 6.00 | 5.00 | 5.00 | 7.00 | 8.00 | 4.53 |
| Compound 11 | 6.00 | 6.00 | 5.00 | 5.,00 | 7.00 | 6.00 | 5.18 |
| A-30380 | 6.00 | 6.00 | 5.00 | 5.00 | 8.00 | 9.00 | 5.26 |
| Compound 7 | 6.00 | 5.00 | 5.00 | 5.00 | 6.00 | 7.00 | 4.79 |
| Compound 9 | 6.00 | 6.00 | 5.00 | 5.00 | 7.00 | 7.00 | 4.00 |
| SKF-104856 | 7.00 | 7.00 | 6.00 | 7.00 | 6.00 | 7.00 | 4.68 |
| S-Niguidipine | ND | ND | ND | ND | 7.00 | 7.00 | 8.04 |
| Compound 8 | 6.00 | 5.00 | 5.00 | 5.00 | 7.00 | 6.00 | 6.87 |
| Compound 2 | 7.00 | 6.00 | 5.00 | 5.00 | 6.00 | 7.00 | 6.13 |

ND = Not Determined
As used herein, SEM means the standard error of the mean.

TABLE 4

CROSS REACTIVITY OF ALPHA-1 ANTAGONISTS AT CLONED HUMAN RECEPTORS

| Ki(nM) Compound | Alpha-1 Adrenergic | | | | | | Alpha-2 Adrenergic | | | | |
|---|---|---|---|---|---|---|---|---|---|---|---|
| | α1A MEAN | SEM | α1B MEAN | SEM | α1C MEAN | SEM | a2a MEAN | SEM | a2b MEAN | SEM | a2c MEAN |
| Terazosin | 3 | 0.31 | 2 | 0.17 | 7 | 0.31 | 550 | 123 | 31 | 5 | 226 |
| Prazosin | 0.33 | 0.07 | 0.55 | 0.14 | 0.59 | 0.10 | 174 | 33 | 23 | 8 | 22 |
| 5-Methylurapidil | 16 | 3 | 170 | 35 | 4 | 0.92 | 234 | 35 | 42 | 4 | 132 |
| Indoramin | 182 | 31 | 41 | 7 | 4 | 0.75 | 11482 | 3719 | 1905 | 556 | 4026 |
| Compound 11 | 155 | 20 | 72 | 23 | 4 | 1.41 | 134 | 3 | 126 | 14 | 120 |
| A-30340 | 32 | 7 | 14 | 3 | 3 | 0.62 | 204 | 30 | 427 | 38 | 589 |
| Compound 7 | 151 | 10 | 46 | 15 | 4 | 0.05 | 646 | 15 | 851 | 19 | 813 |
| Compound 9 | 759 | 257 | 174 | 83 | 15 | 0.99 | 1585 | 0 | 2042 | | 1259 |
| SKF-104856 | 3 | 0.36 | 32 | 13 | 25 | 10.35 | 50 | 38 | 3 | 2 | 25 |
| S-Niguidipine | 191 | 32 | 85 | 21 | 2 | 0.43 | 446 | | 5754 | | 372 |
| Compound 8 | 302 | 39 | 85 | 7 | 3 | 0.29 | 1023 | 111 | 759 | 51 | 1698 |
| Compound 2 | 1047 | 106 | 269 | 65 | 3 | 0.33 | 3311 | 109 | 1375 | 103 | 2316 |

| Ki(nM) Compound | SEM | Histamine | | | | Calcium Channel | |
|---|---|---|---|---|---|---|---|
| | | H1 MEAN | SEM | H2 MEAN | SEM | MEAN | SEM |
| Terazosin | 15 | 100000 | | 9120 | 4222 | 6457 | |
| Prazosin | 3 | 100000 | | 6457 | 2383 | 26915 | |
| 5-Methyluradipil | 9 | 6918 | 1548 | 33884 | 6342 | | |
| Indoramin | 770 | 43 | 11 | 2344 | 384 | 29512 | |
| Compound 11 | 13 | 1620 | 41 | 35 | 0.08 | 6607 | |
| A-30340 | 39 | 933 | 209 | 1698 | 318 | 5495 | |
| Compound 7 | 19 | 26 | 6 | 955 | 22 | 16218 | |
| Compound 9 | | 31 | 9 | 3631 | 680 | 10000 | |
| SKF-104856 | 10 | 2570 | 383 | 1445 | 127 | 20893 | |
| S-Niguidipine | 63 | 164 | 11 | 575 | 86 | 9 | 1 |
| Compound 8 | 316 | 214 | 40 | 776 | 84 | 135 | 35 |
| Compound 2 | 341 | 49 | 6 | 33 | 4 | 741 | 17 |

| Ki(nM) Compound | 5HT1Da | 5HT1Db | 5HT1E | 5HT1F | 5HT2 | D2 | Ca Chann |
|---|---|---|---|---|---|---|---|
| Terazosin | 1000 | 1000 | 10000 | 10000 | 10000 | 10000 | 6457 |
| Prazosin | 10000 | 10000 | ND | ND | 1000 | 10000 | 26915 |
| 5-Methylurapidil | 50 | 161 | ND | ND | 1000 | 10000 | |
| Indoramin | 1000 | 1000 | 10000 | 10000 | 100 | 10 | 29512 |
| Compound 11 | 1000 | 1000 | 10000 | 10000 | 100 | 1000 | 6607 |
| A-30360 | 1000 | 1000 | 10000 | 10000 | 10 | 1 | 5495 |
| Compound 7 | 1000 | 10000 | 10000 | 10000 | 1000 | 100 | 16218 |
| Compound 9 | 1000 | 1000 | 10000 | 10000 | 100 | 100 | 100000 |
| SKF-104856 | 100 | 100 | 1000 | 100 | 1000 | 100 | 20893 |

TABLE 4-continued

CROSS REACTIVITY OF ALPHA-1 ANTAGONISTS AT CLONED HUMAN RECEPTORS

| | | | | | | | |
|---|---|---|---|---|---|---|---|
| S-Niguidipine | ND | ND | ND | ND | 100 | 100 | 9 |
| Compound 8 | 1000 | 10000 | 10000 | 10000 | 100 | 1000 | 135 |
| Compound 2 | 100 | 1000 | 10000 | 10000 | 1000 | 100 | 741 |

ND = Not Determined

TABLE 5

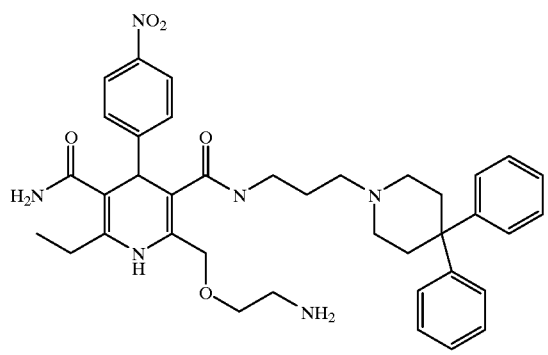

Alpha adrenergic 'Ki (nM)' 'Fold selectivity hAlpha1c' 'n' RECEPTORS SUMMARY

| | hA1a | hA1b | hA1c | rA1a | rA1b | rA1c | dA1a | dA1b | dA1c | Opioid |
|---|---|---|---|---|---|---|---|---|---|---|
| Ki | 514.34 | 326.21 | 0.47 | | | | 3659 | 1467.80 | 22.05 | |
| Fold | 1089.6 | 691.0 | 1 | | | 1 | 166.0 | 66.6 | 1 | 0.0 |
| n | 4 | 4 | 3 | | | | 3 | 3 | 3 | |

| | | | | | | | Calcium % i.a. | | Calcium % i.a. | | Calcium % i.a. | |
|---|---|---|---|---|---|---|---|---|---|---|---|---|
| | hA2a | hA2b | hA2c | hH1 | hH2 | Ca Chl | Ag hA1a | Ant. hA1a | Ag. hA1b | Ant. hA1b | Ag. hA1c | Ant. hA1c |
| Ki | 402.72 | 901.57 | 203.86 | 184.08 | 462.38 | 19216.16 % i.a. | 0.5 | 11.0 | 2.0 | 14.5 | 0.5 | 99.5 |
| Fold | 853.1 | 1909.9 | 431.9 | 389.9 | 979.5 | 40706.8 sem | 0.4 | 4.2 | 0.0 | 4.6 | 0.4 | 0.4 |
| n | 2 | 3 | 3 | 2 | 2 | 3 n | 2 | 2 | 2 | 2 | 2 | 2 |

| | hD1 | hD2 | hD3 | hD5 | h5HT-A | h5HT-B | h5HT-C | h5HT-D | h5HT-E | h5HT-F | h5HT-G |
|---|---|---|---|---|---|---|---|---|---|---|---|
| Ki | 8156.43 | 991.97 | 70957.78 | 58143.34 | 1083.21 | 2398.83 | | | | 3801.89 | 502.82 |
| Fold | 17278.3 | 2101.4 | 150314.2 | 123168.6 | 2294.6 | 5081.6 | 0.0 | 0.0 | 0.0 | 8053.8 | 1065.1 |
| n | 2 | 2 | 2 | 2 | 1 | 1 | | | | 1 | 1 |

TABLE 6

COMPARISON OF ALPHA-1 ANTAGONIST CROSSREACTIVITY BETWEEN HUMAN NEURONAL RECEPTORS AND HUMAN ALPHA-1C RECEPTOR
(ANTAGONIST Ki NEURONAL RECEPTOR)
(ANTAGONIST Ki ALPHA-1C ADRENERGIC RECEPTOR)

| | Alpha-1 Adrenergic | | | | | | Alpha-2 Adrenergic | | | | |
|---|---|---|---|---|---|---|---|---|---|---|---|
| Compound | α1A MEAN | SEM | α1B MEAN | SEM | α1C MEAN | SEM | a2a MEAN | SEM | a2b MEAN | SEM | a2c MEAN |
| Terazosin | 1 | 0 | 0 | 0 | 1 | | 79 | 16 | 4 | 1 | 33 |
| Prazosin | 1 | 0 | 1 | 0 | 1 | | 295 | 55 | 39 | 14 | 38 |
| 5-Methylurapidil | 4 | 1 | 38 | 8 | 1 | | 52 | 8 | 9 | 1 | 30 |
| Indoramin | 41 | 7 | 9 | 2 | 1 | | 2570 | 833 | 427 | 125 | 1349 |
| Compound 11 | 35 | 5 | 17 | 5 | 1 | | 32 | 1 | 29 | 3 | 28 |
| A-30360 | 11 | 2 | 5 | 1 | 1 | | 68 | 10 | 141 | 12 | 195 |
| Compound 7 | 40 | 3 | 17 | 4 | 1 | | 170 | 4 | 224 | 5 | 214 |
| Compound 9 | 51 | 17 | 12 | 6 | 1 | | 107 | 0 | 138 | 0 | 85 |
| SKF-104856 | 0 | 0 | 1 | 1 | 1 | | 2 | 2 | 0 | 0 | 1 |
| S-Niguidipine | 107 | 16 | 40 | 12 | 1 | | 363 | 0 | 3236 | 0 | 209 |
| Compound 8 | 91 | 12 | 26 | 2 | 1 | | 309 | 24 | 219 | 15 | 515 |
| Compound 2 | 276 | 116 | 200 | 48 | 1 | | 2455 | 393 | 871 | 77 | 699 |

TABLE 6-continued

| | | Histamine | | | | Calcium | |
| | | H1 | | H2 | | Channel | |
| Compound | SEM | MEAN | SEM | MEAN | SEM | MEAN | SEM |
|---|---|---|---|---|---|---|---|
| Terazosin | 2 | 14454 | | 1318 | 410 | 933 | |
| Prazosin | 6 | 169824 | | 10965 | 4046 | 45709 | |
| 5-Methylurapidil | 2 | 1549 | 347 | 7586 | 1420 | | |
| Indoramin | 174 | 10 | 2 | 525 | 88 | 6607 | |
| Compound 11 | 3 | 417 | 9 | 8 | 0 | 1514 | |
| A-30360 | 13 | 309 | 69 | 562 | 105 | 1820 | |
| Compound 7 | 5 | 7 | 2 | 251 | 6 | 4264 | |
| Compound 9 | 0 | 3 | 1 | 245 | 46 | 6761 | |
| SKF-104856 | 0 | 102 | 15 | 58 | 5 | 832 | |
| S-Niguidipine | 47 | 93 | 6 | 324 | 48 | 5 | 1 |
| Compound 8 | 96 | 65 | 12 | 234 | 25 | 41 | 10 |
| Compound 2 | 253 | 31 | 5 | 25 | 5 | 330 | 13 |

| | ALPHA-1a SELECTIVITY | | | | | | |
| Compound | 5HT1Da | 5HT1Db | 5HT1E | 5HT1F | 5HT2 | D2 | Ca Chann |
|---|---|---|---|---|---|---|---|
| Terazosin | 145 | 145 | 1445 | 1455 | 1455 | 1455 | 933 |
| Prazosin | 16982 | 16982 | ND | ND | 1698 | 16982 | 45709 |
| 5-Methylurapidil | 11 | 34 | ND | ND | 224 | 2239 | |
| Indoramin | 224 | 224 | 2239 | 2239 | 22 | 2 | 6607 |
| Compound 11 | 229 | 299 | 2291 | 2291 | 23 | 229 | 1514 |
| A-30360 | 331 | 331 | 3311 | 3311 | 3 | 0 | 1820 |
| Compound 7 | 263 | 2630 | 2630 | 2630 | 263 | 26 | 4266 |
| Compound 9 | 68 | 68 | 676 | 676 | 7 | 7 | 6761 |
| SKF-104856 | 4 | 4 | 40 | 4 | 40 | 4 | 832 |
| S-Niguidipine | ND | ND | ND | ND | 56 | 56 | 5 |
| Compound 8 | 302 | 3020 | 3020 | 3020 | 30 | 302 | 41 |
| Compound 2 | 74 | 741 | 7413 | 7413 | 741 | 74 | 650 |

ND = Not Determined

EXAMPLE 11

Functional Properties of $\alpha_1$ Antagonists on Rat Orthostatic Hypertension

We have identified a large series of compounds (well over 150 compounds, data not shown) which exemplify the hereinabove described properties of antagonists highly selective for the $\alpha_{1C}$ adrenergic receptor. That is, these compounds are highly selective Alpha 1c antagonists which have less than 10 fold the affinity at cloned human Alpha 1a, Alpha 1b, Alpha 2a, Alpha 2b, Alpha 2C, Histamine H1, Dopamine D2 and Serotonin receptors. In addition, these compounds have 10 fold lower affinity at calcium channels (data not shown). We designated five of these highly selective antagonists for the $\alpha_{1C}$ adrenergic receptor as drugs 21–25 and used them to further characterize highly selective antagonists for the $\alpha_{1C}$ adrenergic receptor.

In addition, a number of these selective alpha 1c antagonists are potent at inhibiting the phenylephrine stimulated contraction of human prostate as described in Example 11. This is a well established protocol for evaluation the efficacy of drugs which may be useful for the treatment of BPH.

In addition, we have examined a number of selective alpha 1c antagonists in an in vivo canine prostate model (Felson, D., et al., J. Urol., 141, 1230–1233 (1989))which is a well characterized model for evaluating the efficacy of BPH drugs (data not shown). In this model, selective alpha 1c antagnists increase urethral pressure at doses which do not produce significant decreases in canine blood pressure. In contrast, nonselective alpha 1 antagonists do not have as large a separation between the effects on urethral pressure and the effects on blood pressure. These observations support our premise that a selective alpha 1c antagonist will have a better safety profile than a nonselective alpha 1 antagonist. We have further characterized selective alpha 1c antagonists in a rat orthostatic hypotension model. This model gives information on the vascular effects of drugs which may be indicative of their ability to produce dizziness in patients (Hieble, J. P., et al., *Cardiovascular Pharmacology*, 15, 845 (1990)). Our objective was to characterize the effects of selective alpha 1c antagonists on rat orthostatic hypotension and contrast the results with those obtained using nonselective alpha 1 antagonists.

Methods

Rat Orthostatic Hypotension Model

Adult male Sprague-Dawley normotensive rats were anesthetized with sodium pentobarbital (45 mg/kg, i.v.). The femoral vein and artery of the right hindllimb were cannulated for drug administration and blood pressure monitoring, respectively. Heart rate was determined by a cardiotachometer triggered by the blood pressure pulse. The rats were secured in the supine position to a board that could be tilted 90 degrees. When blood pressure and heart rate had stabilized, the rats were subjected to a 90 degree vertical (head up) tilt for 60 seconds. Changes in blood pressure and heart rate from pre-tilt levels were monitored continuously. The rats were returned to the supine position and blood pressure and heart rate were allowed to stabilize. Either an antagonist selective for the $\alpha_{1C}$ adrenergic receptor (designated drug 21, 22, 23, 24 or 25), an antagonist nonselective for the $\alpha_{1C}$ adrenergic receptor (Prazosin or Terazosin) or saline was then administered through venous cannula, either as an i.v. bolus or as an infusion, when blood pressure had stabilized, the rats were subjected to a second tilt and blood pressure and heart rate were recorded as described above. Most saline treated rats typically exhibit a greater ability to return their blood pressure toward pre-tilt levels during the second tilt. Data from the second tilt are used in statistical analysis.

Results

Table 7 shows that while nonselective alpha 1 antagonists produce significant effects on orthostatic hypotension, selective alpha 1 c antagonists do not produce significant effects. More specifically, Prazosin and Terazosin consistently cause orthostasis at the lowest dose (10 ug/kg) and, in some rats, in a dose-dependent manner. Drug 21 causes orthostasis only at the highest dose (1000 ug/kg) in 2 out of 4 rats, while the other antagonists selective for the $\alpha_{1C}$ adrenergic receptor causes no orthostasis at the highest dose. Placebo and 22, 23, 24, 25 did not induce orthostasis at any dose. Taken all together, this is a positive result since it is believed that orthostatic hypotension contributes to the dizziness ovserved clinically with noselective alpha 1 antagonists. This further supports our premise that a selective alpha 1c antagonist will have a better safety profile than a nonselective alpha 1 antagonist.

TABLE 7

Summary of Studies on Drug Effects on Orthostasis

| Drug | n | Dose 1 10 μg/kg | | Dose 2 100 μg/kg | | Dose 3 1000 μg/kg | | Notes |
|---|---|---|---|---|---|---|---|---|
| | | orthostatic fall in BP | BP fall | orthostatic fall in BP | BP fall | orthostatic fall in BP | BP fall | |
| Placebo (DMSO) | 3 | − | − | − | − | − | − | |
| Prezosin | 4 | + | + | ++ or ++ | ++ | ++ or +++ | +++ | |
| Terazosin | 2 | + | + | ++ or +++ | ++ | ++ or +++ | +++ | |
| 21 | 4 | − | + | − | ++ | +/− | +++ | (+ in 2/4) |
| 22 | 3 | − | + | − | ++ | − | +++ | |
| 23 | 6 | − | − | − | − | − | + | |
| 24 | 6 | − | − | − | +/− | − | + | |
| 25 | 4 | − | − | +/− | − | − | − | (+ in 1/4) |

+ and − mean positive or negative findings, respectively
+, ++ and +++ are relative to doses of the same drug but not compared to other drugs
+/− positive findings found in some rats

What is claimed is:

1. A method of treating benign prostatic hyperplasia in a subject which comprises administering to the subject a therapeutically effective amount of an antagonist which binds to a human $\alpha_{1C}$ adrenergic receptor with a binding affinity at least 691-fold higher than the binding affinity with which the antagonist binds to a human $\alpha_{1B}$ adrenergic receptor.

2. A method of treating benign prostatic hyperplasia in a subject which comprises administering to the subject a therapeutically effective amount of an antagonist which binds to a human $\alpha_{1C}$ adrenergic receptor with a binding affinity at least 1089-fold higher than the binding affinity with which the antagonist binds to a human $\alpha_{1A}$ adrenergic receptor.

3. The method of claim 1, wherein the binding affinity of the antagonist is at least 91-fold higher for the human $\alpha_{1C}$ adrenergic receptor than it is for a human $\alpha_{1A}$ adrenergic receptor.

4. The method of claim 2, wherein the binding affinity of the antagonist is at least 28-fold higher for the human $\alpha_{1C}$ adrenergic receptor than it is for any human $\alpha_2$ adrenergic receptor.

5. The method of claim 1, wherein the binding affinity of the antagonist for the human $\alpha_{1C}$ adrenergic receptor is (I) at least 91-fold higher than it is for the human $\alpha_{1A}$ adrenergic receptor, (ii) at least 65-fold higher than it is for the human histamine $H_1$ receptor, and (iii) at least 229-fold higher than it is for the human $\alpha_2$ adrenergic receptor.

6. The method of claim 1, wherein the binding affinity of the antagonist for the human $\alpha_{1C}$ adrenergic receptor is at least 41-fold higher than it is for any calcium channel.

7. The method of claim 1, wherein the binding affinity of the antagonist for the human $\alpha_{1C}$ adrenergic receptor is at least 234-fold higher than it is for a human histamine $H_2$ receptor.

8. The method of claim 1, wherein the binding affinity of the antagonist for the human $\alpha_{1C}$ adrenergic receptor is at least 30-fold higher than it is for a human serotonin receptor.

9. The method of claim 1 or 2, wherein the antagonist does not cause an orthostatis fall in blood pressure.

10. The method of claim 9, wherein the antagonist additionally does not cause an orthostatic fall in blood pressure in rats at a dosage of 10 micrograms of antagonist per kilogram of rat.

11. A method of inhibiting contraction of prostatic tissue which comprises contacting the prostate tissue with an effective contraction-inhibiting amount of an antagonist which binds to a human $\alpha_{1C}$ adrenergic receptor with a binding affinity at least 691-fold higher than the binding affinity with which the antagonist binds to a human $\alpha_{1B}$ adrenergic receptor.

12. A method of inhibiting contraction of prostatic tissue which comprises contacting the prostate tissue with an effective contraction-inhibiting amount of an antagonist which binds to a human $\alpha_{1C}$ adrenergic receptor with a binding affinity at least 1089-fold higher than the binding affinity with which the antagonist binds to a human $\alpha_{1A}$ adrenergic receptor.

13. The method of claim 11, wherein the binding affinity of the antagonist is at least 91-fold higher for the human $\alpha_{1C}$ adrenergic receptor than it is for any human $\alpha_{1A}$ adrenergic receptor.

14. The method of claim 12, wherein the binding affinity of the antagonist is at least 28-fold higher for the human $\alpha_{1C}$ adrenergic receptor than it is for a human $\alpha_2$ adrenergic receptor.

15. The method of claim 11, wherein the binding affinity of the antagonist for the human $\alpha_{1C}$ adrenergic receptor is (I) at least 91-fold higher than it is for the human $\alpha_{1A}$ adrenergic receptor, (ii) at least 65-fold higher than it is for the human histamine $H_1$ receptor, and (iii) at least 229-fold higher than it is for the human $\alpha_2$ adrenergic receptor.

16. The method of claim 11, wherein the binding affinity of the antagonist for the human $\alpha_{1C}$ adrenergic receptor is at least 41-fold higher than it is for any calcium channel.

17. The method of claim 11, wherein the binding affinity of the antagonist for the human $\alpha_{1C}$ adrenergic receptor is at least 234-fold higher than it is for a human histamine $H_2$ receptor.

18. The method of claim 11, wherein the binding affinity of the antagonist for the human $\alpha_{1C}$ adrenergic receptor is at least 30-fold higher than it is for a human serotonin receptor.

19. The method of claim 11 or 12, wherein the antagonist does not cause an orthostatic fall in blood pressure.

20. The method of claim 19, wherein the antagonist additionally does not cause an orthostatic fall in blood pressure in rats at a dosage of 10 micrograms of antagonist per kilogram of rat.

* * * * *

UNITED STATES PATENT AND TRADEMARK OFFICE
CERTIFICATE OF CORRECTION

PATENT NO.    : 5,990,128
DATED         : November 23, 1999
INVENTOR(S)   : Charles Gluchowski, et al.

Page 1 of 2

It is certified that error appears in the above-identified patent and that said Letters Patent is hereby corrected as shown below:

Column 7,
Line 1 "alc" should read -- $\alpha_{1c}$ --

Column 15,
Line 23, "(60%o" should read -- (60%) --

Column 18,
Line 57, "Rhf" should read -- THF --

Column 19,
Line 20, "pectral" should read -- spectral --
Line 29, "rnl" should read -- ml --

Column 27,
Line 26, "line s" should read -- lines --
Line 33, "partiaL" should read -- partial --

Table 1,
"6.51 should read -- 6.57 --
"A-30380" should read -- A-30360 --
"7.88" should read -- 7. 86 --
"SKF-104858" should read -- SKF-104856 --

Table 2,
"S-Niguidipine" should read -- S-Niguldipine --

UNITED STATES PATENT AND TRADEMARK OFFICE
CERTIFICATE OF CORRECTION

PATENT NO. : 5,990,128
DATED : November 23, 1999
INVENTOR(S) : Charles Gluchowski, et al.

It is certified that error appears in the above-identified patent and that said Letters Patent is hereby corrected as shown below:

Table 3,
"8.48" should read -- 8.46 --
"8.74" should read -- 6.74 --
"8.81" should read -- 6.81 --
"8.82" should read -- 6.82 --
"8.12" should read -- 6.12 --
"8.48" should read -- 8.46 --
"SKF-104858" should read -- SKF-104856 --
"S-Niguidipine" should read -- S-Niguldipine --
"8.12" should read -- 6.72 --
"S-Niguidipine" should read -- S-Niguldipine --

Table 4,
"S-Niguidipine" should read -- S-Niguldipine --

Table 6,
"S-Niguidipine" should read -- S-Niguldipine --

Signed and Sealed this

Twenty-first Day of August, 2001

Attest:

*Nicholas P. Godici*

NICHOLAS P. GODICI
*Attesting Officer*  *Acting Director of the United States Patent and Trademark Office*

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2140 base pairs
      (B) TYPE: nucleic acid
      (C) STRANDEDNESS: single
      (D) TOPOLOGY: unknown (ii) MOLECULE TYPE: DNA (genomic)

(iii) HYPOTHETICAL: N (iv) ANTI-SENSE: N (ix) FEATURE:
      (A) NAME/KEY: CDS
      (B) LOCATION: 178..1893
      (D) OTHER INFORMATION:

(xi) SEQUENCE DESCRIPTION: SEQ ID NO:1:

```
CCGGGCCAGG CACGTCCGCT CTCGGACAGC CGCTCCGCGT CACAGGAACT TGGGCAGGAC        60

CCGACGGGAC CCGTGCGCGG AGCTGCATCT GGAGCCCCGC GGCTATGCCC TGTGCTCCCC       120

TCCTGCCGGC CGCTCGTTCT GTGCCCCCGG CCCGGCCACC GACGGCCGCG CGTTGAG         177

ATG ACT TTC CGC GAT CTC CTG AGC GTC AGT TTC GAG GGA CCC CGC CCG        225
Met Thr Phe Arg Asp Leu Leu Ser Val Ser Phe Glu Gly Pro Arg Pro
 1               5                  10                  15

GAC AGC AGC GCA GGG GGC TCC AGC GCG GGC GGC GGG GGC AGC GCG            273
Asp Ser Ser Ala Gly Gly Ser Ser Ala Gly Gly Gly Gly Ser Ala
             20                  25                  30

GGC GGC GCG GCC CCC TCG GAG GGC CCG GCG GTG GGC GGC GTG CCG GGG        321
```

| | | | | | | | | | | | | | | | |
|---|---|---|---|---|---|---|---|---|---|---|---|---|---|---|---|
| | Gly | Gly | Ala | Ala | Pro | Ser | Glu | Gly | Pro | Ala | Val | Gly | Gly | Val | Pro Gly |
| | | | 35 | | | | 40 | | | | 45 | | | | |

```
GGC GCG GGC GGC GGC GGC GGC GTG GTG GGC GCA GGC AGC GGC GAG GAC      369
Gly Ala Gly Gly Gly Gly Gly Val Val Gly Ala Gly Ser Gly Glu Asp
 50              55              60

AAC CGG AGC TCC GCG GGG GAG CCG GGG AGC GCG GGC GCG GGC GGC GAC      417
Asn Arg Ser Ser Ala Gly Glu Pro Gly Ser Ala Gly Ala Gly Gly Asp
 65              70              75              80

GTG AAT GGC ACG GCG GCC GTC GGG GGA CTG GTG GTG AGC GCG CAG GGC      465
Val Asn Gly Thr Ala Ala Val Gly Gly Leu Val Val Ser Ala Gln Gly
             85              90              95

GTG GGC GTG GGC GTC TTC CTG GCA GCC TTC ATC CTT ATG GCC GTG GCA      513
Val Gly Val Gly Val Phe Leu Ala Ala Phe Ile Leu Met Ala Val Ala
            100             105             110

GGT AAC CTG CTT GTC ATC CTC TCA GTG GCC TGC AAC CGC CAC CTG CAG      561
Gly Asn Leu Leu Val Ile Leu Ser Val Ala Cys Asn Arg His Leu Gln
        115             120             125

ACC GTC ACC AAC TAT TTC ATC GTG AAC CTG GCC GTG GCC GAC CTG CTG      609
Thr Val Thr Asn Tyr Phe Ile Val Asn Leu Ala Val Ala Asp Leu Leu
        130             135             140

CTG AGC GCC ACC GTA CTG CCC TTC TCG GCC ACC ATG GAG GTT CTG GGC      657
Leu Ser Ala Thr Val Leu Pro Phe Ser Ala Thr Met Glu Val Leu Gly
145             150             155             160

TTC TGG GCC TTT GGC CGC GCC TTC TGC GAC GTA TGG GCC GCC GTG GAC      705
Phe Trp Ala Phe Gly Arg Ala Phe Cys Asp Val Trp Ala Ala Val Asp
            165             170             175

GTG CTG TGC TGC ACG GCC TCC ATC CTC AGC CTC TGC ACC ATC TCC GTG      753
Val Leu Cys Cys Thr Ala Ser Ile Leu Ser Leu Cys Thr Ile Ser Val
        180             185             190

GAC CGG TAC GTG GGC GTG CGC CAC TCA CTC AAG TAC CCA GCC ATC ATG      801
Asp Arg Tyr Val Gly Val Arg His Ser Leu Lys Tyr Pro Ala Ile Met
        195             200             205

ACC GAG CGC AAG GCG GCC GCC ATC CTG GCC CTG CTC TGG GTC GTA GCC      849
Thr Glu Arg Lys Ala Ala Ala Ile Leu Ala Leu Leu Trp Val Val Ala
210             215             220

CTG GTG GTG TCC GTA GGG CCC CTG CTG GGC TGG AAG GAG CCC GTG CCC      897
Leu Val Val Ser Val Gly Pro Leu Leu Gly Trp Lys Glu Pro Val Pro
225             230             235             240

CCT GAC GAG CGC TTC TGC GGT ATC ACC GAG GAG GCG GGC TAC GCT GTC      945
Pro Asp Glu Arg Phe Cys Gly Ile Thr Glu Glu Ala Gly Tyr Ala Val
            245             250             255

TTC TCC TCC GTG TGC TCC TTC TAC CTG CCC ATG GCG GTC ATC GTG GTC      993
Phe Ser Ser Val Cys Ser Phe Tyr Leu Pro Met Ala Val Ile Val Val
        260             265             270

ATG TAC TGC CGC GTG TAC GTG GTC GCG CGC AGC ACC ACG CGC AGC CTC     1041
Met Tyr Cys Arg Val Tyr Val Val Ala Arg Ser Thr Thr Arg Ser Leu
        275             280             285

GAG GCA GGC GTC AAG CGC GAG CGA GGC AAG GCC TCC GAG GTG GTG CTG     1089
Glu Ala Gly Val Lys Arg Glu Arg Gly Lys Ala Ser Glu Val Val Leu
        290             295             300

CGC ATC CAC TGT CGC GGC GCG GCC ACG GGC GCC GAC GGG GCG CAC GGC     1137
Arg Ile His Cys Arg Gly Ala Ala Thr Gly Ala Asp Gly Ala His Gly
305             310             315             320

ATG CGC AGC GCC AAG GGC CAC ACC TTC CGC AGC TCG CTC TCC GTG CGC     1185
Met Arg Ser Ala Lys Gly His Thr Phe Arg Ser Ser Leu Ser Val Arg
            325             330             335

CTG CTC AAG TTC TCC CGT GAG AAG AAA GCG GCC AAG ACT CTG GCC ATC     1233
Leu Leu Lys Phe Ser Arg Glu Lys Lys Ala Ala Lys Thr Leu Ala Ile
            340             345             350

GTC GTG GGT GTC TTC GTG CTC TGC TGG TTC CCT TTC TTC TTT GTC CTG     1281
```

```
Val Val Gly Val Phe Val Leu Cys Trp Phe Pro Phe Phe Val Leu
        355                 360                 365

CCG CTC GGC TCC TTG TTC CCG CAG CTG AAG CCA TCG GAG GGC GTC TTC         1329
Pro Leu Gly Ser Leu Phe Pro Gln Leu Lys Pro Ser Glu Gly Val Phe
        370                 375                 380

AAG GTC ATC TTC TGG CTC GGC TAC TTC AAC AGC TGC GTG AAC CCG CTC         1377
Lys Val Ile Phe Trp Leu Gly Tyr Phe Asn Ser Cys Val Asn Pro Leu
385                 390                 395                 400

ATC TAC CCC TGT TCC AGC CGC GAG TTC AAG CGC GCC TTC CTC CGT CTC         1425
Ile Tyr Pro Cys Ser Ser Arg Glu Phe Lys Arg Ala Phe Leu Arg Leu
                405                 410                 415

CTG CGC TGC CAG TGC CGT CGT CGC CGG CGC CGC CGC CCT CTC TGG CGT         1473
Leu Arg Cys Gln Cys Arg Arg Arg Arg Arg Arg Arg Pro Leu Trp Arg
                420                 425                 430

GTC TAC GGC CAC CAC TGG CGG GCC TCC ACC AGC GGC CTG CGC CAG GAC         1521
Val Tyr Gly His His Trp Arg Ala Ser Thr Ser Gly Leu Arg Gln Asp
                435                 440                 445

TGC GCC CCG AGT TCG GGC GAC GCG CCC CCC GGA GCG CCG CTG GCC CTC         1569
Cys Ala Pro Ser Ser Gly Asp Ala Pro Pro Gly Ala Pro Leu Ala Leu
        450                 455                 460

ACC GCG CTC CCC GAC CCC GAC CCC GAA CCC CCA GGC ACG CCC GAG ATG         1617
Thr Ala Leu Pro Asp Pro Asp Pro Glu Pro Pro Gly Thr Pro Glu Met
465                 470                 475                 480

CAG GCT CCG GTC GCC AGC CGT CGA AAG CCA CCC AGC GCC TTC CGC GAG         1665
Gln Ala Pro Val Ala Ser Arg Arg Lys Pro Pro Ser Ala Phe Arg Glu
                485                 490                 495

TGG AGG CTG CTG GGG CCG TTC CGG AGA CCC ACG ACC CAG CTG CGC GCC         1713
Trp Arg Leu Leu Gly Pro Phe Arg Arg Pro Thr Thr Gln Leu Arg Ala
                500                 505                 510

AAA GTC TCC AGC CTG TCG CAC AAG ATC CGC GCC GGG GGC GCG CAG CGC         1761
Lys Val Ser Ser Leu Ser His Lys Ile Arg Ala Gly Gly Ala Gln Arg
                515                 520                 525

GCA GAG GCA GCG TGC GCC CAG CGC TCA GAG GTG GAG GCT GTG TCC CTA         1809
Ala Glu Ala Ala Cys Ala Gln Arg Ser Glu Val Glu Ala Val Ser Leu
        530                 535                 540

GGC GTC CCA CAC GAG GTG GCC GAG GGC GCC ACC TGC CAG GCC TAC GAA         1857
Gly Val Pro His Glu Val Ala Glu Gly Ala Thr Cys Gln Ala Tyr Glu
545                 550                 555                 560

TTG GCC GAC TAC AGC AAC CTA CGG GAG ACC GAT ATT TAAGGACCCC              1903
Leu Ala Asp Tyr Ser Asn Leu Arg Glu Thr Asp Ile
                565                 570

AGAGCTAGGC CGCGGAGTGT GCTGGGCTTG GGGGTAAGGG GGACCAGAGA GGCGGGCTGG       1963

TGTTCTAAGA GCCCCCGTGC AAATCGGAGA CCCGGAAACT GATCAGGGCA GCTGCTCTGT       2023

GACATCCCTG AGGAACTGGG CAGAGCTTGA GGCTGGAGCC CTTGAAAGGT GAAAAGTAGT       2083

GGGGCCCCCT GCTGGACTCA GGTGCCCAGA ACTCTTTTCT TAGAAGGGAG AGGCTGC         2140

(2) INFORMATION FOR SEQ ID NO:2:

(i) SEQUENCE CHARACTERISTICS:
        (A) LENGTH: 572 amino acids
        (B) TYPE: amino acid
        (D) TOPOLOGY: linear (ii) MOLECULE TYPE: protein (xi) SEQUENCE DESCRIPTION: SEQ ID NO:2:

Met Thr Phe Arg Asp Leu Leu Ser Val Ser Phe Glu Gly Pro Arg Pro
 1               5                  10                  15

Asp Ser Ser Ala Gly Gly Ser Ser Ala Gly Gly Gly Gly Ser Ala
                20                  25                  30
```

```
Gly Gly Ala Ala Pro Ser Glu Gly Pro Ala Val Gly Gly Val Pro Gly
            35                  40                  45

Gly Ala Gly Gly Gly Gly Val Val Gly Ala Gly Ser Gly Glu Asp
        50                  55                  60

Asn Arg Ser Ser Ala Gly Glu Pro Gly Ser Ala Gly Ala Gly Gly Asp
 65                  70                  75                  80

Val Asn Gly Thr Ala Ala Val Gly Gly Leu Val Val Ser Ala Gln Gly
                85                  90                  95

Val Gly Val Gly Val Phe Leu Ala Ala Phe Ile Leu Met Ala Val Ala
                100                 105                 110

Gly Asn Leu Leu Val Ile Leu Ser Val Ala Cys Asn Arg His Leu Gln
            115                 120                 125

Thr Val Thr Asn Tyr Phe Ile Val Asn Leu Ala Val Ala Asp Leu Leu
        130                 135                 140

Leu Ser Ala Thr Val Leu Pro Phe Ser Ala Thr Met Glu Val Leu Gly
145                 150                 155                 160

Phe Trp Ala Phe Gly Arg Ala Phe Cys Asp Val Trp Ala Ala Val Asp
                165                 170                 175

Val Leu Cys Cys Thr Ala Ser Ile Leu Ser Leu Cys Thr Ile Ser Val
                180                 185                 190

Asp Arg Tyr Val Gly Val Arg His Ser Leu Lys Tyr Pro Ala Ile Met
            195                 200                 205

Thr Glu Arg Lys Ala Ala Ala Ile Leu Ala Leu Leu Trp Val Val Ala
        210                 215                 220

Leu Val Val Ser Val Gly Pro Leu Leu Gly Trp Lys Glu Pro Val Pro
225                 230                 235                 240

Pro Asp Glu Arg Phe Cys Gly Ile Thr Glu Glu Ala Gly Tyr Ala Val
                245                 250                 255

Phe Ser Ser Val Cys Ser Phe Tyr Leu Pro Met Ala Val Ile Val Val
                260                 265                 270

Met Tyr Cys Arg Val Tyr Val Val Ala Arg Ser Thr Thr Arg Ser Leu
            275                 280                 285

Glu Ala Gly Val Lys Arg Glu Arg Gly Lys Ala Ser Glu Val Val Leu
        290                 295                 300

Arg Ile His Cys Arg Gly Ala Ala Thr Gly Ala Asp Gly Ala His Gly
305                 310                 315                 320

Met Arg Ser Ala Lys Gly His Thr Phe Arg Ser Ser Leu Ser Val Arg
                325                 330                 335

Leu Leu Lys Phe Ser Arg Glu Lys Lys Ala Ala Lys Thr Leu Ala Ile
                340                 345                 350

Val Val Gly Val Phe Val Leu Cys Trp Phe Pro Phe Phe Val Leu
            355                 360                 365

Pro Leu Gly Ser Leu Phe Pro Gln Leu Lys Pro Ser Glu Gly Val Phe
        370                 375                 380

Lys Val Ile Phe Trp Leu Gly Tyr Phe Asn Ser Cys Val Asn Pro Leu
385                 390                 395                 400

Ile Tyr Pro Cys Ser Ser Arg Glu Phe Lys Arg Ala Phe Leu Arg Leu
                405                 410                 415

Leu Arg Cys Gln Cys Arg Arg Arg Arg Arg Arg Pro Leu Trp Arg
            420                 425                 430

Val Tyr Gly His His Trp Arg Ala Ser Thr Ser Gly Leu Arg Gln Asp
            435                 440                 445

Cys Ala Pro Ser Ser Gly Asp Ala Pro Pro Gly Ala Pro Leu Ala Leu
```

```
            450                 455                 460
Thr Ala Leu Pro Asp Pro Asp Pro Glu Pro Pro Gly Thr Pro Glu Met
465                 470                 475                 480

Gln Ala Pro Val Ala Ser Arg Arg Lys Pro Pro Ser Ala Phe Arg Glu
                485                 490                 495

Trp Arg Leu Leu Gly Pro Phe Arg Arg Pro Thr Thr Gln Leu Arg Ala
                500                 505                 510

Lys Val Ser Ser Leu Ser His Lys Ile Arg Ala Gly Ala Gln Arg
                515                 520                 525

Ala Glu Ala Ala Cys Ala Gln Arg Ser Glu Val Glu Ala Val Ser Leu
                530                 535                 540

Gly Val Pro His Glu Val Ala Glu Gly Ala Thr Cys Gln Ala Tyr Glu
545                 550                 555                 560

Leu Ala Asp Tyr Ser Asn Leu Arg Glu Thr Asp Ile
                565                 570
```

(2) INFORMATION FOR SEQ ID NO:3:

(i) SEQUENCE CHARACTERISTICS:
        (A) LENGTH: 1738 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: N (iv) ANTI-SENSE: N (ix) FEATURE:
        (A) NAME/KEY: CDS
        (B) LOCATION: 124..1683
        (D) OTHER INFORMATION:

(xi) SEQUENCE DESCRIPTION: SEQ ID NO:3:

```
GCCAGGAGGG CGCCTCTGGG AAGAAGACCA CGGGGGAAGC AAAGTTTCAG GGCAGCTGAG       60

GAGCCTTCGC CGCAGCCCTT CCGAGCCCAA TCATCCCCCA GGCTATGGAG GGCGGACTCT      120

AAG ATG AAT CCC GAC CTG GAC ACC GGC CAC AAC ACA TCA GCA CCT GCC        168
    Met Asn Pro Asp Leu Asp Thr Gly His Asn Thr Ser Ala Pro Ala
    1               5                   10                  15

CAC TGG GGA GAG TTG AAA AAT GCC AAC TTC ACT GGC CCC AAC CAG ACC        216
His Trp Gly Glu Leu Lys Asn Ala Asn Phe Thr Gly Pro Asn Gln Thr
                20                  25                  30

TCG AGC AAC TCC ACA CTG CCC CAG CTG GAC ATC ACC AGG GCC ATC TCT        264
Ser Ser Asn Ser Thr Leu Pro Gln Leu Asp Ile Thr Arg Ala Ile Ser
                35                  40                  45

GTG GGC CTG GTG CTG GGC GCC TTC ATC CTC TTT GCC ATC GTG GGC AAC        312
Val Gly Leu Val Leu Gly Ala Phe Ile Leu Phe Ala Ile Val Gly Asn
            50                  55                  60

ATC CTA GTC ATC TTG TCT GTG GCC TGC AAC CGG CAC CTG CGG ACG CCC        360
Ile Leu Val Ile Leu Ser Val Ala Cys Asn Arg His Leu Arg Thr Pro
65                  70                  75

ACC AAC TAC TTC ATT GTC AAC CTG GCC ATG GCC GAC CTG CTG TTG AGC        408
Thr Asn Tyr Phe Ile Val Asn Leu Ala Met Ala Asp Leu Leu Leu Ser
80                  85                  90                  95

TTC ACC GTC CTG CCC TTC TCA GCG GCC CTA GAG GTG CTC GGC TAC TGG        456
Phe Thr Val Leu Pro Phe Ser Ala Ala Leu Glu Val Leu Gly Tyr Trp
                100                 105                 110

GTG CTG GGG CGG ATC TTC TGT GAC ATC TGG GCA GCC GTG GAT GTC CTG        504
Val Leu Gly Arg Ile Phe Cys Asp Ile Trp Ala Ala Val Asp Val Leu
                115                 120                 125
```

```
TGC TGC ACA GCG TCC ATT CTG AGC CTG TGC GCC ATC TCC ATC GAT CGC        552
Cys Cys Thr Ala Ser Ile Leu Ser Leu Cys Ala Ile Ser Ile Asp Arg
        130                 135                 140

TAC ATC GGG GTG CGC TAC TCT CTG CAG TAT CCC ACG CTG GTC ACC CGG        600
Tyr Ile Gly Val Arg Tyr Ser Leu Gln Tyr Pro Thr Leu Val Thr Arg
145                 150                 155

AGG AAG GCC ATC TTG GCG CTG CTC AGT GTC TGG GTC TTG TCC ACC GTC        648
Arg Lys Ala Ile Leu Ala Leu Leu Ser Val Trp Val Leu Ser Thr Val
160                 165                 170                 175

ATC TCC ATC GGG CCT CTC CTT GGG TGG AAG GAG CCG GCA CCC AAC GAT        696
Ile Ser Ile Gly Pro Leu Leu Gly Trp Lys Glu Pro Ala Pro Asn Asp
            180                 185                 190

GAC AAG GAG TGC GGG GTC ACC GAA GAA CCC TTC TAT GCC CTC TTC TCC        744
Asp Lys Glu Cys Gly Val Thr Glu Glu Pro Phe Tyr Ala Leu Phe Ser
        195                 200                 205

TCT CTG GGC TCC TTC TAC ATC CCT CTG GCG GTC ATT CTA GTC ATG TAC        792
Ser Leu Gly Ser Phe Tyr Ile Pro Leu Ala Val Ile Leu Val Met Tyr
    210                 215                 220

TGC CGT GTC TAT ATA GTG GCC AAG AGA ACC ACC AAG AAC CTA GAG GCA        840
Cys Arg Val Tyr Ile Val Ala Lys Arg Thr Thr Lys Asn Leu Glu Ala
225                 230                 235

GGA GTC ATG AAG GAG ATG TCC AAC TCC AAG GAG CTG ACC CTG AGG ATC        888
Gly Val Met Lys Glu Met Ser Asn Ser Lys Glu Leu Thr Leu Arg Ile
240                 245                 250                 255

CAT TCC AAG AAC TTT CAC GAG GAC ACC CTT AGC AGT ACC AAG GCC AAG        936
His Ser Lys Asn Phe His Glu Asp Thr Leu Ser Ser Thr Lys Ala Lys
            260                 265                 270

GGC CAC AAC CCC AGG AGT TCC ATA GCT GTC AAA CTT TTT AAG TTC TCC        984
Gly His Asn Pro Arg Ser Ser Ile Ala Val Lys Leu Phe Lys Phe Ser
        275                 280                 285

AGG GAA AAG AAA GCA GCT AAG ACG TTG GGC ATT GTG GTC GGT ATG TTC       1032
Arg Glu Lys Lys Ala Ala Lys Thr Leu Gly Ile Val Val Gly Met Phe
    290                 295                 300

ATC TTG TGC TGG CTA CCC TTC TTC ATC GCT CTA CCG CTT GGC TCC TTG       1080
Ile Leu Cys Trp Leu Pro Phe Phe Ile Ala Leu Pro Leu Gly Ser Leu
305                 310                 315

TTC TCC ACC CTG AAG CCC CCC GAC GCC GTG TTC AAG GTG GTG TTC TGG       1128
Phe Ser Thr Leu Lys Pro Pro Asp Ala Val Phe Lys Val Val Phe Trp
320                 325                 330                 335

CTG GGC TAC TTC AAC AGC TGC CTC AAC CCC ATC ATC TAC CCA TGC TCC       1176
Leu Gly Tyr Phe Asn Ser Cys Leu Asn Pro Ile Ile Tyr Pro Cys Ser
            340                 345                 350

AGC AAG GAG TTC AAG CGC GCT TTC GTG CGC ATC CTC GGG TGC CAG TGC       1224
Ser Lys Glu Phe Lys Arg Ala Phe Val Arg Ile Leu Gly Cys Gln Cys
        355                 360                 365

CGC GGC CGC GGC CGC CGC CGA CGC CGC CGC CGC CGT CGC CTG GGC GGC       1272
Arg Gly Arg Gly Arg Arg Arg Arg Arg Arg Arg Arg Leu Gly Gly
    370                 375                 380

TGC GCC TAC ACC TAC CGG CCG TGG ACG CGC GGC GGC TCG CTG GAG CGC       1320
Cys Ala Tyr Thr Tyr Arg Pro Trp Thr Arg Gly Gly Ser Leu Glu Arg
385                 390                 395

TCG CAG TCG CGC AAG GAC TCG CTG GAC GAC AGC GGC AGC TGC CTG AGC       1368
Ser Gln Ser Arg Lys Asp Ser Leu Asp Asp Ser Gly Ser Cys Leu Ser
400                 405                 410                 415

GGC AGC CAG CGG ACC CTG CCC TCG GCC TCG CCG AGC CCG GGC TAC CTG       1416
Gly Ser Gln Arg Thr Leu Pro Ser Ala Ser Pro Ser Pro Gly Tyr Leu
            420                 425                 430

GGC CGC GGC GCG CCA CCG CCA GTC GAG CTG TGC GCC TTC CCC GAG TGG       1464
Gly Arg Gly Ala Pro Pro Pro Val Glu Leu Cys Ala Phe Pro Glu Trp
        435                 440                 445
```

```
AAG GCG CCC GGC GCC CTC CTG AGC CTG CCC GCG CCT GAG CCC CCC GGC          1512
Lys Ala Pro Gly Ala Leu Leu Ser Leu Pro Ala Pro Glu Pro Pro Gly
            450                 455                 460

CGC CGC GGC CGC CAC GAC TCG GGC CCG CTC TTC ACC TTC AAG CTC CTG          1560
Arg Arg Gly Arg His Asp Ser Gly Pro Leu Phe Thr Phe Lys Leu Leu
465                 470                 475

ACC GAG CCC GAG AGC CCC GGG ACC GAC GGC GGC GCC AGC AAC GGA GGC          1608
Thr Glu Pro Glu Ser Pro Gly Thr Asp Gly Gly Ala Ser Asn Gly Gly
480                 485                 490                 495

TGC GAG GCC GCG GCC GAC GTG GCC AAC GGG CAG CCG GGC TTC AAA AGC          1656
Cys Glu Ala Ala Ala Asp Val Ala Asn Gly Gln Pro Gly Phe Lys Ser
            500                 505                 510

AAC ATG CCC CTG GCG CCC GGG CAG TTT TAGGGCCCCC GTGCGCAGCT                1703
Asn Met Pro Leu Ala Pro Gly Gln Phe
            515                 520

TTCTTTCCCT GGGGAGGAAA ACATCGTGGG GGGGA                                   1738
```

(2) INFORMATION FOR SEQ ID NO:4:

(i) SEQUENCE CHARACTERISTICS:
        (A) LENGTH: 520 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asn Pro Asp Leu Asp Thr Gly His Asn Thr Ser Ala Pro Ala His
1               5                   10                  15

Trp Gly Glu Leu Lys Asn Ala Asn Phe Thr Gly Pro Asn Gln Thr Ser
                20                  25                  30

Ser Asn Ser Thr Leu Pro Gln Leu Asp Ile Thr Arg Ala Ile Ser Val
            35                  40                  45

Gly Leu Val Leu Gly Ala Phe Ile Leu Phe Ala Ile Val Gly Asn Ile
50                  55                  60

Leu Val Ile Leu Ser Val Ala Cys Asn Arg His Leu Arg Thr Pro Thr
65                  70                  75                  80

Asn Tyr Phe Ile Val Asn Leu Ala Met Ala Asp Leu Leu Leu Ser Phe
                85                  90                  95

Thr Val Leu Pro Phe Ser Ala Ala Leu Glu Val Leu Gly Tyr Trp Val
            100                 105                 110

Leu Gly Arg Ile Phe Cys Asp Ile Trp Ala Ala Val Asp Val Leu Cys
        115                 120                 125

Cys Thr Ala Ser Ile Leu Ser Leu Cys Ala Ile Ser Ile Asp Arg Tyr
130                 135                 140

Ile Gly Val Arg Tyr Ser Leu Gln Tyr Pro Thr Leu Val Thr Arg Arg
145                 150                 155                 160

Lys Ala Ile Leu Ala Leu Leu Ser Val Trp Val Leu Ser Thr Val Ile
                165                 170                 175

Ser Ile Gly Pro Leu Leu Gly Trp Lys Glu Pro Ala Pro Asn Asp Asp
            180                 185                 190

Lys Glu Cys Gly Val Thr Glu Glu Pro Phe Tyr Ala Leu Phe Ser Ser
        195                 200                 205

Leu Gly Ser Phe Tyr Ile Pro Leu Ala Val Ile Leu Val Met Tyr Cys
210                 215                 220

Arg Val Tyr Ile Val Ala Lys Arg Thr Thr Lys Asn Leu Glu Ala Gly
225                 230                 235                 240
```

```
Val Met Lys Glu Met Ser Asn Ser Lys Glu Leu Thr Leu Arg Ile His
            245                 250                 255

Ser Lys Asn Phe His Glu Asp Thr Leu Ser Ser Thr Lys Ala Lys Gly
            260                 265                 270

His Asn Pro Arg Ser Ser Ile Ala Val Lys Leu Phe Lys Phe Ser Arg
            275                 280                 285

Glu Lys Lys Ala Ala Lys Thr Leu Gly Ile Val Val Gly Met Phe Ile
            290                 295                 300

Leu Cys Trp Leu Pro Phe Phe Ile Ala Leu Pro Leu Gly Ser Leu Phe
305                 310                 315                 320

Ser Thr Leu Lys Pro Pro Asp Ala Val Phe Lys Val Val Phe Trp Leu
            325                 330                 335

Gly Tyr Phe Asn Ser Cys Leu Asn Pro Ile Ile Tyr Pro Cys Ser Ser
            340                 345                 350

Lys Glu Phe Lys Arg Ala Phe Val Arg Ile Leu Gly Cys Gln Cys Arg
            355                 360                 365

Gly Arg Gly Arg Arg Arg Arg Arg Arg Arg Arg Leu Gly Gly Cys
            370                 375                 380

Ala Tyr Thr Tyr Arg Pro Trp Thr Arg Gly Gly Ser Leu Glu Arg Ser
385                 390                 395                 400

Gln Ser Arg Lys Asp Ser Leu Asp Asp Ser Gly Ser Cys Leu Ser Gly
            405                 410                 415

Ser Gln Arg Thr Leu Pro Ser Ala Ser Pro Ser Pro Gly Tyr Leu Gly
            420                 425                 430

Arg Gly Ala Pro Pro Val Glu Leu Cys Ala Phe Pro Glu Trp Lys
            435                 440                 445

Ala Pro Gly Ala Leu Leu Ser Leu Pro Ala Pro Glu Pro Pro Gly Arg
            450                 455                 460

Arg Gly Arg His Asp Ser Gly Pro Leu Phe Thr Phe Lys Leu Leu Thr
465                 470                 475                 480

Glu Pro Glu Ser Pro Gly Thr Asp Gly Gly Ala Ser Asn Gly Gly Cys
            485                 490                 495

Glu Ala Ala Ala Asp Val Ala Asn Gly Gln Pro Gly Phe Lys Ser Asn
            500                 505                 510

Met Pro Leu Ala Pro Gly Gln Phe
            515                 520

(2) INFORMATION FOR SEQ ID NO:5:

(i) SEQUENCE CHARACTERISTICS:
        (A) LENGTH: 1639 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: N (iv) ANTI-SENSE: N (ix) FEATURE:
        (A) NAME/KEY: CDS
        (B) LOCATION: 126..1523
        (D) OTHER INFORMATION:

(xi) SEQUENCE DESCRIPTION: SEQ ID NO:5:

CCAGCCAAAC CACTGGCAGG CTCCCTCCAG CCGAGACCTT TTATTCCCGG CTCCCGAGCT      60

CCGCCTCCGC GCCAGCCCGG GAGGTGGCCC TGACAGCCGG ACCTCGCCCG GCCCCGGCTG     120
```

```
GGACC ATG GTG TTT CTC TCG GGA AAT GCT TCC GAC AGC TCC AAC TGC         167
      Met Val Phe Leu Ser Gly Asn Ala Ser Asp Ser Ser Asn Cys
      1               5                   10

ACC CAA CCG CCG GCA CCG GTG AAC ATT TCC AAG GCC ATT CTG CTC GGG       215
Thr Gln Pro Pro Ala Pro Val Asn Ile Ser Lys Ala Ile Leu Leu Gly
15              20                  25                  30

GTG ATC TTG GGG GGC CTC ATT CTT TTC GGG GTG CTG GGT AAC ATC CTA       263
Val Ile Leu Gly Gly Leu Ile Leu Phe Gly Val Leu Gly Asn Ile Leu
            35                  40                  45

GTG ATC CTC TCC GTA GCC TGT CAC CGA CAC CTG CAC TCA GTC ACG CAC       311
Val Ile Leu Ser Val Ala Cys His Arg His Leu His Ser Val Thr His
                50                  55                  60

TAC TAC ATC GTC AAC CTG GCG GTG GCC GAC CTC CTG CTC ACC TCC ACG       359
Tyr Tyr Ile Val Asn Leu Ala Val Ala Asp Leu Leu Leu Thr Ser Thr
                    65                  70                  75

GTG CTG CCC TTC TCC GCC ATC TTC GAG GTC CTA GGC TAC TGG GCC TTC       407
Val Leu Pro Phe Ser Ala Ile Phe Glu Val Leu Gly Tyr Trp Ala Phe
80              85                  90

GGC AGG GTC TTC TGC AAC ATC TGG GCG GCA GTG GAT GTG CTG TGC TGC       455
Gly Arg Val Phe Cys Asn Ile Trp Ala Ala Val Asp Val Leu Cys Cys
95              100                 105                 110

ACC GCG TCC ATC ATG GGC CTC TGC ATC ATC TCC ATC GAC CGC TAC ATC       503
Thr Ala Ser Ile Met Gly Leu Cys Ile Ile Ser Ile Asp Arg Tyr Ile
                115                 120                 125

GGC GTG AGC TAC CCG CTG CGC TAC CCA ACC ATC GTC ACC CAG AGG AGG       551
Gly Val Ser Tyr Pro Leu Arg Tyr Pro Thr Ile Val Thr Gln Arg Arg
            130                 135                 140

GGT CTC ATG GCT CTG CTC TGC GTC TGG GCA CTC TCC CTG GTC ATA TCC       599
Gly Leu Met Ala Leu Leu Cys Val Trp Ala Leu Ser Leu Val Ile Ser
            145                 150                 155

ATT GGA CCC CTG TTC GGC TGG AGG CAG CCG GCC CCC GAG GAC GAG ACC       647
Ile Gly Pro Leu Phe Gly Trp Arg Gln Pro Ala Pro Glu Asp Glu Thr
160             165                 170

ATC TGC CAG ATC AAC GAG GAG CCG GGC TAC GTG CTC TTC TCA GCG CTG       695
Ile Cys Gln Ile Asn Glu Glu Pro Gly Tyr Val Leu Phe Ser Ala Leu
175             180                 185                 190

GGC TCC TTC TAC CTG CCT CTG GCC ATC ATC CTG GTC ATG TAC TGC CGC       743
Gly Ser Phe Tyr Leu Pro Leu Ala Ile Ile Leu Val Met Tyr Cys Arg
                195                 200                 205

GTC TAC GTG GTG GCC AAG AGG GAG AGC CGG GGC CTC AAG TCT GGC CTC       791
Val Tyr Val Val Ala Lys Arg Glu Ser Arg Gly Leu Lys Ser Gly Leu
            210                 215                 220

AAG ACC GAC AAG TCG GAC TCG GAG CAA GTG ACG CTC CGC ATC CAT CGG       839
Lys Thr Asp Lys Ser Asp Ser Glu Gln Val Thr Leu Arg Ile His Arg
            225                 230                 235

AAA AAC GCC CCG GCA GGA GGC AGC GGG ATG GCC AGC GCC AAG ACC AAG       887
Lys Asn Ala Pro Ala Gly Gly Ser Gly Met Ala Ser Ala Lys Thr Lys
240                 245                 250

ACG CAC TTC TCA GTG AGG CTC CTC AAG TTC TCC CGG GAG AAG AAA GCG       935
Thr His Phe Ser Val Arg Leu Leu Lys Phe Ser Arg Glu Lys Lys Ala
255             260                 265                 270

GCC AAA ACG CTG GGC ATC GTG GTC GGC TGC TTC GTC CTC TGC TGG CTG       983
Ala Lys Thr Leu Gly Ile Val Val Gly Cys Phe Val Leu Cys Trp Leu
                275                 280                 285

CCT TTT TTC TTA GTC ATG CCC ATT GGG TCT TTC TTC CCT GAT TTC AAG       1031
Pro Phe Phe Leu Val Met Pro Ile Gly Ser Phe Phe Pro Asp Phe Lys
            290                 295                 300

CCC TCT GAA ACA GTT TTT AAA ATA GTA TTT TGG CTC GGA TAT CTA AAC       1079
Pro Ser Glu Thr Val Phe Lys Ile Val Phe Trp Leu Gly Tyr Leu Asn
305                 310                 315
```

| | |
|---|---|
| AGC TGC ATC AAC CCC ATC ATA TAC CCA TGC TCC AGC CAA GAG TTC AAA<br>Ser Cys Ile Asn Pro Ile Ile Tyr Pro Cys Ser Ser Gln Glu Phe Lys<br>320                                  325                                330 | 1127 |
| AAG GCC TTT CAG AAT GTC TTG AGA ATC CAG TGT CTC TGC AGA AAG CAG<br>Lys Ala Phe Gln Asn Val Leu Arg Ile Gln Cys Leu Cys Arg Lys Gln<br>335                                  340                                345                                350 | 1175 |
| TCT TCC AAA CAT GCC CTG GGC TAC ACC CTG CAC CCG CCC AGC CAG GCC<br>Ser Ser Lys His Ala Leu Gly Tyr Thr Leu His Pro Pro Ser Gln Ala<br>                    355                                360                                365 | 1223 |
| GTG GAA GGG CAA CAC AAG GAC ATG GTG CGC ATC CCC GTG GGA TCA AGA<br>Val Glu Gly Gln His Lys Asp Met Val Arg Ile Pro Val Gly Ser Arg<br>              370                                  375                                380 | 1271 |
| GAG ACC TTC TAC AGG ATC TCC AAG ACG GAT GGC GTT TGT GAA TGG AAA<br>Glu Thr Phe Tyr Arg Ile Ser Lys Thr Asp Gly Val Cys Glu Trp Lys<br>385                                  390                                395 | 1319 |
| TTT TTC TCT TCC ATG CCC CGT GGA TCT GCC AGG ATT ACA GTG TCC AAA<br>Phe Phe Ser Ser Met Pro Arg Gly Ser Ala Arg Ile Thr Val Ser Lys<br>400                                  405                                410 | 1367 |
| GAC CAA TCC TCC TGT ACC ACA GCC CGG GTG AGA AGT AAA AGC TTT TTG<br>Asp Gln Ser Ser Cys Thr Thr Ala Arg Val Arg Ser Lys Ser Phe Leu<br>415                                  420                                425                                430 | 1415 |
| CAG GTC TGC TGC TGT GTA GGG CCC TCA ACC CCC AGC CTT GAC AAG AAC<br>Gln Val Cys Cys Cys Val Gly Pro Ser Thr Pro Ser Leu Asp Lys Asn<br>                                  435                                440                                445 | 1463 |
| CAT CAA GTT CCA ACC ATT AAG GTC CAC ACC ATC TCC CTC AGT GAG AAC<br>His Gln Val Pro Thr Ile Lys Val His Thr Ile Ser Leu Ser Glu Asn<br>              450                                  455                                460 | 1511 |
| GGG GAG GAA GTC TAGGACAGGA AAGATGCAGA GGAAAGGGGA ATATCTTAGG<br>Gly Glu Glu Val<br>              465 | 1563 |
| TACCATACCC TGGAGTTCTA GAGGATTCCT CGACAAGCTT ATTCCGATCC AGACATGATA | 1623 |
| GATACATTGA TGAGTT | 1639 |

(2) INFORMATION FOR SEQ ID NO:6:

(i) SEQUENCE CHARACTERISTICS:
        (A) LENGTH: 466 amino acids
        (B) TYPE: amino acid
        (D) TOPOLOGY: linear (ii) MOLECULE TYPE: protein (xi) SEQUENCE DESCRIPTION: SEQ ID NO:6:

```
Met Val Phe Leu Ser Gly Asn Ala Ser Asp Ser Ser Asn Cys Thr Gln
 1               5                  10                  15

Pro Pro Ala Pro Val Asn Ile Ser Lys Ala Ile Leu Leu Gly Val Ile
                20                  25                  30

Leu Gly Gly Leu Ile Leu Phe Gly Val Leu Gly Asn Ile Leu Val Ile
            35                  40                  45

Leu Ser Val Ala Cys His Arg His Leu His Ser Val Thr His Tyr Tyr
    50                  55                  60

Ile Val Asn Leu Ala Val Ala Asp Leu Leu Leu Thr Ser Thr Val Leu
65                  70                  75                  80

Pro Phe Ser Ala Ile Phe Glu Val Leu Gly Tyr Trp Ala Phe Gly Arg
                85                  90                  95

Val Phe Cys Asn Ile Trp Ala Ala Val Asp Val Leu Cys Cys Thr Ala
                100                 105                 110

Ser Ile Met Gly Leu Cys Ile Ile Ser Ile Asp Arg Tyr Ile Gly Val
            115                 120                 125
```

-continued

```
Ser Tyr Pro Leu Arg Tyr Pro Thr Ile Val Thr Gln Arg Arg Gly Leu
    130             135             140

Met Ala Leu Leu Cys Val Trp Ala Leu Ser Leu Val Ile Ser Ile Gly
145             150             155             160

Pro Leu Phe Gly Trp Arg Gln Pro Ala Pro Glu Asp Glu Thr Ile Cys
            165             170             175

Gln Ile Asn Glu Glu Pro Gly Tyr Val Leu Phe Ser Ala Leu Gly Ser
            180             185             190

Phe Tyr Leu Pro Leu Ala Ile Ile Leu Val Met Tyr Cys Arg Val Tyr
        195             200             205

Val Val Ala Lys Arg Glu Ser Arg Gly Leu Lys Ser Gly Leu Lys Thr
        210             215             220

Asp Lys Ser Asp Ser Glu Gln Val Thr Leu Arg Ile His Arg Lys Asn
225             230             235             240

Ala Pro Ala Gly Gly Ser Gly Met Ala Ser Ala Lys Thr Lys Thr His
            245             250             255

Phe Ser Val Arg Leu Leu Lys Phe Ser Arg Glu Lys Lys Ala Ala Lys
            260             265             270

Thr Leu Gly Ile Val Val Gly Cys Phe Val Leu Cys Trp Leu Pro Phe
        275             280             285

Phe Leu Val Met Pro Ile Gly Ser Phe Phe Pro Asp Phe Lys Pro Ser
        290             295             300

Glu Thr Val Phe Lys Ile Val Phe Trp Leu Gly Tyr Leu Asn Ser Cys
305             310             315             320

Ile Asn Pro Ile Ile Tyr Pro Cys Ser Ser Gln Glu Phe Lys Lys Ala
            325             330             335

Phe Gln Asn Val Leu Arg Ile Gln Cys Leu Cys Arg Lys Gln Ser Ser
            340             345             350

Lys His Ala Leu Gly Tyr Thr Leu His Pro Pro Ser Gln Ala Val Glu
            355             360             365

Gly Gln His Lys Asp Met Val Arg Ile Pro Val Gly Ser Arg Glu Thr
        370             375             380

Phe Tyr Arg Ile Ser Lys Thr Asp Gly Val Cys Glu Trp Lys Phe Phe
385             390             395             400

Ser Ser Met Pro Arg Gly Ser Ala Arg Ile Thr Val Ser Lys Asp Gln
            405             410             415

Ser Ser Cys Thr Thr Ala Arg Val Arg Ser Lys Ser Phe Leu Gln Val
            420             425             430

Cys Cys Cys Val Gly Pro Ser Thr Pro Ser Leu Asp Lys Asn His Gln
        435             440             445

Val Pro Thr Ile Lys Val His Thr Ile Ser Leu Ser Glu Asn Gly Glu
    450             455             460

Glu Val
465
```